(12) United States Patent
Lee et al.

(10) Patent No.: US 12,174,464 B2
(45) Date of Patent: Dec. 24, 2024

(54) CONTACT LENS HAVING SENSORS AND METHODS FOR PRODUCING THE SAME

(71) Applicant: Purdue Research Foundation, West Lafayette, IN (US)

(72) Inventors: Chi Hwan Lee, West Lafayette, IN (US); Bryan William Boudouris, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 561 days.

(21) Appl. No.: 17/365,734

(22) Filed: Jul. 1, 2021

(65) Prior Publication Data

US 2022/0004026 A1 Jan. 6, 2022

Related U.S. Application Data

(60) Provisional application No. 63/047,899, filed on Jul. 2, 2020.

(51) Int. Cl.

| | |
|---|---|
| *G02C 7/04* | (2006.01) |
| *A61B 5/00* | (2006.01) |
| *A61B 5/268* | (2021.01) |
| *A61B 5/297* | (2021.01) |
| *C08G 65/26* | (2006.01) |
| *B82Y 5/00* | (2011.01) |

(52) U.S. Cl.
CPC .............. *G02C 7/049* (2013.01); *A61B 5/268* (2021.01); *A61B 5/297* (2021.01); *A61B 5/6821* (2013.01); *C08G 65/2636* (2013.01); *G02C 7/047* (2013.01); *A61B 2560/0468* (2013.01); *B82Y 5/00* (2013.01)

(58) Field of Classification Search
CPC .......... G02C 7/049; G02C 7/047; G02C 7/04; A61B 5/268; A61B 5/297; A61B 5/6821; A61B 2560/0468; C08G 65/2636; B82Y 5/00
See application file for complete search history.

(56) References Cited

U.S. PATENT DOCUMENTS

| | | | |
|---|---|---|---|
| 2007/0188710 A1* | 8/2007 | Hetling ................. | A61B 5/398 351/221 |
| 2008/0213460 A1* | 9/2008 | Benter .................. | C08J 7/0427 427/377 |

(Continued)

*Primary Examiner* — William R Alexander
*Assistant Examiner* — Gabriel A Sanz
(74) *Attorney, Agent, or Firm* — Hartman Global IP Law; Gary M. Hartman; Domenica N. S. Hartman

(57) ABSTRACT

A device includes a contact lens, a corneal sensor that includes a circular trace of conduction paths located at or near an outer peripheral edge of the contact lens that surrounds an unobstructed area at a center region of the contact lens, and a connection wire coupled to the corneal sensor and configured to electrically couple to an external data acquisition system. Methods of fabricating the device may include providing a thin device that includes a sensor and a connection wire coupled to the sensor, transferring the sensor to a curvilinear inner surface of a contact lens, feeding the connection wire through the inner surface of the contact lens and out of an outer surface of the contact lens, and performing electrochemical polymerization of a conducting polymer material over the sensor to anchor the sensor to the inner surface of the contact lens.

18 Claims, 18 Drawing Sheets

(56) References Cited

U.S. PATENT DOCUMENTS

| | | | | |
|---|---|---|---|---|
| 2010/0312252 A1* | 12/2010 | Jia | .................. | A61F 9/00754 |
| | | | | 606/29 |
| 2013/0309423 A1* | 11/2013 | Roger | ................ | H01B 1/04 |
| | | | | 428/419 |
| 2014/0002788 A1* | 1/2014 | Otts | .............. | B29D 11/00038 |
| | | | | 29/623.2 |
| 2014/0185010 A1* | 7/2014 | Bernert | ................ | A61B 3/112 |
| | | | | 351/219 |
| 2016/0056417 A1* | 2/2016 | Flitsch | .................. | G02C 7/04 |
| | | | | 429/185 |
| 2018/0045980 A1* | 2/2018 | Linhardt | .......... | B29D 11/00817 |
| 2019/0275326 A1* | 9/2019 | Irazoqui | ............. | A61N 1/36046 |
| 2019/0344076 A1* | 11/2019 | Irazoqui | ................ | G02C 7/04 |
| 2020/0401042 A1* | 12/2020 | Bao | .................... | C09D 187/00 |
| 2021/0305582 A1* | 9/2021 | Wang | .................. | H01M 4/663 |
| 2022/0322995 A1* | 10/2022 | Woo | .................... | G02C 11/04 |

\* cited by examiner

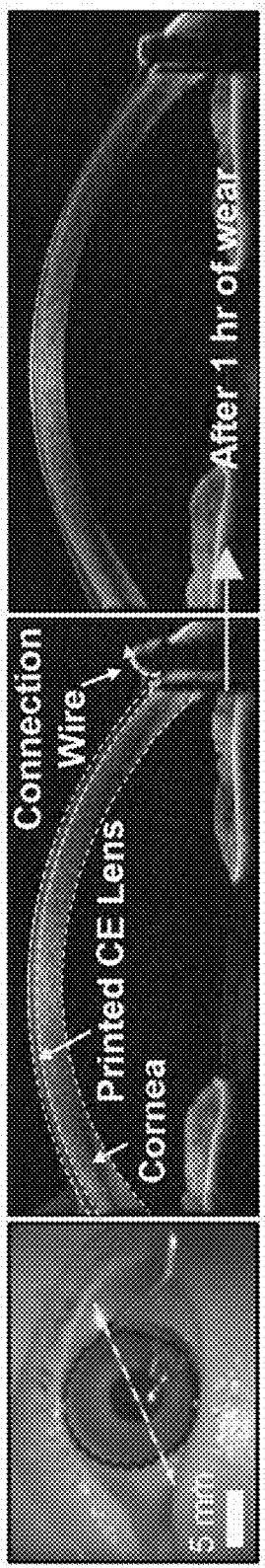
FIG. 4C
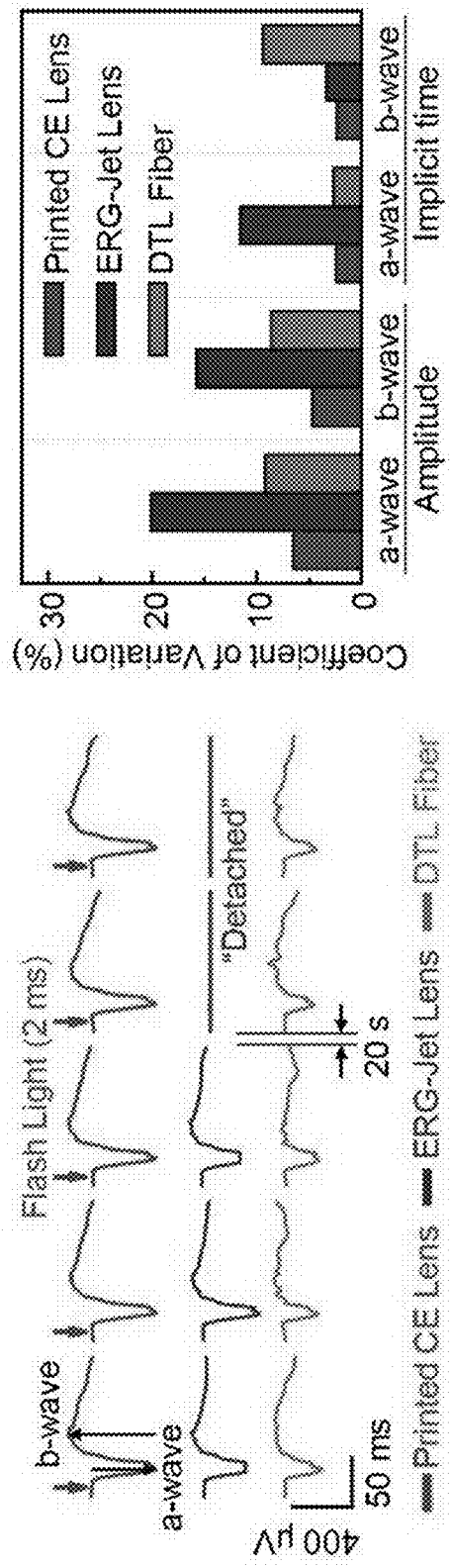
FIG. 4E
FIG. 4D

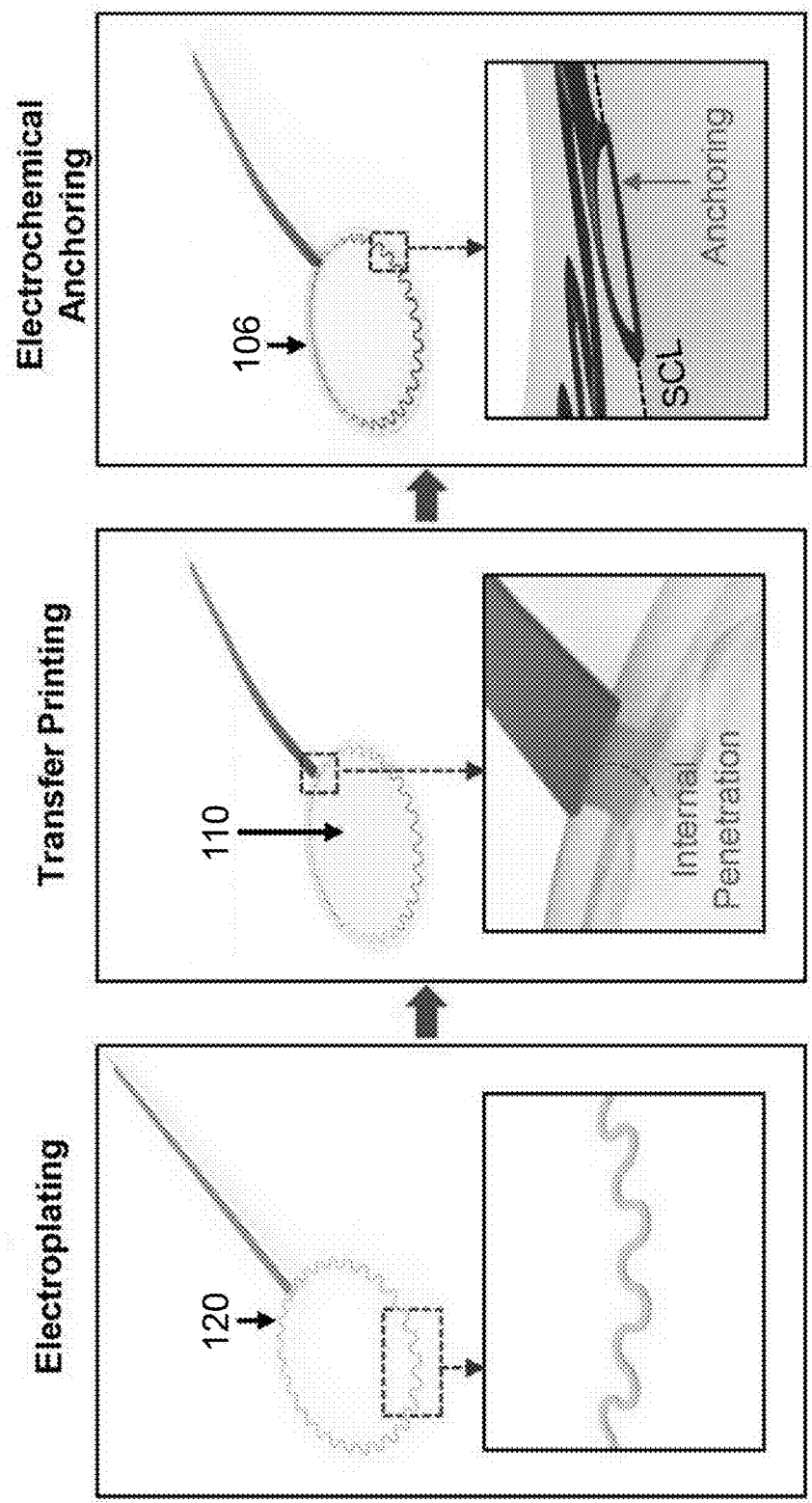

CONTACT LENS HAVING SENSORS AND METHODS FOR PRODUCING THE SAME

CROSS REFERENCE TO RELATED APPLICATIONS

This application claims the benefit of U.S. Provisional Application No. 63/047,899 filed Jul. 2, 2020, the contents of which are incorporated herein by reference.

STATEMENT REGARDING FEDERALLY SPONSORED RESEARCH OR DEVELOPMENT

This invention was made with government support under CMMI 1928784 awarded by the National Science Foundation and under FA9550-19-1-0271 awarded by the Air Force Office of Scientific Research. The government has certain rights in the invention.

BACKGROUND OF THE INVENTION

The present invention generally relates to devices for monitoring physiological parameters. The invention particularly relates to contact lenses comprising corneal sensors suitable for electrodiagnosis, and to methods of producing such lenses.

Electrophysiological activity of the retina in response to a light stimulus, known as an electroretinogram (ERG), can be recorded at the corneal surface in ophthalmic examinations for the diagnosis or early detection of many ocular diseases such as glaucoma, retinitis pigmentosa, diabetic retinopathy, retinoschisis/detachment, and other congenital degenerations. The measurement of ERG signals occurs by contacting a recording electrode directly with either (1) the corneal surface or (2) the bulbar conjunctiva while placing a grounding electrode and a reference electrode on the earlobe and forehead, respectively. The current gold-standard method for measuring ERG signals involves the use of contact lens-type devices (e.g., the ERG-Jet lens) that facilitate direct contact to the corneal surface and thereby enable the recording of ERG signals with relatively higher amplitudes than conjunctival electrodes. However, these devices usually include a thick, rigid contact lens with non-optimal geometries (in particular, anteriorly protruding bumps and large outer curvature for human eyes), resulting in discomfort to both cornea and eyelid despite ocular topical anesthesia. This discomfort is not easily tolerated (especially by children and adults with poor cooperation), and thereby general anesthesia or sedation is often required for these patients. In cases of patient refusal of anesthesia or sedation, a hook-type conjunctival device (e.g., the Dawson Trick Litzkow (DTL) fiber) can alternatively be used. However, the signal quality with these devices is significantly compromised (e.g. less than about 46%) due to its far distance from the cornea, limiting the interpretability of the obtained data.

Newer versions of contact lens-type devices (e.g., the Burian-Allen lens) include a built-in speculum that prevents blinking, and, therefore, enhance the safety and ease of use of these devices from the practitioner standpoint. However, the bulky size of the built-in speculum limits its use only to sedated patients due to severe discomfort. Its use, therefore, is primarily reserved for rare clinical conditions that demand a long-term recording of ERG responses over several hours. Moreover, these devices remain expensive, and, therefore, they are often reused multiple times across different patients. This reuse requires a thorough disinfection process in which the practitioner may lack complete confidence especially with ongoing issues of easily transferable viruses (e.g., the Coronavirus disease 2019 (COVID-19)).

Recent technological advances have led to the development of industrial-grade smart contact lenses, such as the Sensimed TriggerFish lens and the Google smart contact lenses. These devices allow for (1) the continuous monitoring of intraocular pressure (IOP) or biomarkers (e.g., glucose) in tear at the corneal surface and (2) the wireless transmission of the data to the wearer through the use of an integrated circuit (IC) chip. However, the IC chip embedded in these devices is at least greater than 3-fold thicker and greater than 75,000-fold stiffer than a typical soft contact lens (SCL), which results in user discomfort and the risk of corneal hypoxia, especially if worn for a long period of time. Other side effects have been also reported, including foreign body sensation, eye pain, superficial punctate keratitis, corneal epithelial defects, and conjunctival erythema.

More recently, several ongoing research endeavors have helped enable the successful fabrication of a range of flexible sensors on a custom-built contact lens made from several polymers (e.g., hydrogel silicones, Parylene-C, or SU8 resins) and functional nanomaterials (e.g., graphene and metallic nanowires). These newer devices have shown some initial success at the laboratory scale, but their practical application in human eyes remains impeded due to the lack of mechanical reliability (for lens handling, fitting, cleaning, and inadvertent eye rubbing), chemical stability (for long-term lens storage and multiple disinfection cycles), and oxygen transmissibility. Moreover, the custom-built contact lenses used in these devices still suffer from limited wettability or achieving ergonomic curvature, which may affect their long-term wearability for the human eye.

In view of the above, it can be appreciated that there are certain problems, shortcomings or disadvantages associated with the prior art, and that it would be desirable if systems and methods were available for producing safe, easy-to-use, comfortable, cost-effective, and reliable CEs for the measurement of ERG signals in human eyes.

BRIEF DESCRIPTION OF THE INVENTION

The present invention provides eye-wearable devices comprising a contact lens and one or more sensors capable of monitoring physiological parameters including but not limited to the measurement of ERG signals in the human eye, and further provides methods for producing the same.

According to one aspect of the invention, a device is provided that includes a contact lens configured to be located and retained on a user's eye, a corneal sensor that includes a circular trace of conduction paths located at or near an outer peripheral edge of the contact lens that surrounds an unobstructed area at a center region of the contact lens, and a connection wire coupled to the corneal sensor and configured to electrically couple the corneal sensor to an external data acquisition system.

According to another aspect of the invention, a method is provided that includes providing a glass substrate coated with a water-soluble layer, depositing elastomeric materials on the water-soluble layer of the glass substrate to simultaneously form a circular trace and a connection wire coupled to the circular trace, wherein at least one layer of the circular trace and at least one layer of the connection wire define an integral conduction path, removing the water-soluble layer with deionized water to separate the circular trace and the connection wire from the glass substrate, electroplating the circular trace with gold or an alloy thereof, transferring the circular trace to a curvilinear inner surface of a contact lens configured to face a user's eye when worn, feeding the connection wire through the inner surface of the contact lens and out of an outer surface of the contact lens, and performing electrochemical polymerization of a conducting polymer material over the circular trace to anchor the circular trace to the inner surface of the contact lens. The circular trace is configured to function as a corneal sensor and the connection wire is configured to couple the corneal sensor to an external data acquisition system.

According to another aspect of the invention, a method is provided that includes providing a thin device that includes a sensor and a connection wire coupled to the sensor, transferring the sensor to a curvilinear inner surface of a contact lens configured to face a user's eye when worn, feeding the connection wire through the inner surface of the contact lens and out of an outer surface of the contact lens, and performing electrochemical polymerization of a conducting polymer material over the sensor to anchor the sensor to the inner surface of the contact lens. The connection wire is configured to couple the sensor to an external electrical system.

Technical effects of the device and methods described above preferably include the ability to produce eye-wearable devices capable of continuously monitoring various physiological parameters to diagnose or detect diseases, including ocular diseases.

Other aspects and advantages of this invention will be appreciated from the following detailed description.

BRIEF DESCRIPTION OF THE DRAWINGS

FIG. 1A represents an ERG recording in response to a light stimulus from a human eye using the printed CE lens. FIG. 1B represents the printed CE lens, with inset images highlighting the embedded encapsulation and anchoring layers (top panel) and its seamless integration with the elastomeric connection wire (bottom panel). FIG. 1C includes images of am exemplary printed CE lens, with inset images highlighting the embedded serpentine layout (top panel) and its seamless integration with the elastomeric connection wire (bottom panel). FIG. 1D shows cross-sectional microscope images of the printed CE lens. FIG. 1E represents surface topology of the printed CE lens with and without a PEDOT layer.

FIG. 2A shows average stress-strain curves for the printed CE lens, bare lens, printed CE without the SCL, and elastomeric connection wire. FIG. 2B shows relative change in resistance ($\Delta R/R_0$) of the elastomeric connection wire under stretching up to 350%. The inset images show the stretched connection wire.

FIG. 3A shows flipping, FIG. 3B shows folding, FIG. 3C shows stretching (up to 40%), and FIG. 3D shows expanding (up to 10%). The right column shows the corresponding FEA results of the printed CE without the SCL.

FIGS. 4A through 4E represent real-time ERG recordings in a human eye. FIG. 4A represents measurement setting for ERG recordings using a Ganzfeld stimulator in scotopic conditions. FIG. 4B shows images of the eye worn with the printed CE lens (top panel) by comparisons with the ERG-Jet lens (middle panel) and DTL fiber (bottom panel). The yellow circles denote the 4 built-in bumps of the ERG-Jet lens. The white dotted line denotes the outer trace of the DTL fiber. FIG. 4C shows images (left inset) and the corresponding anterior segment ocular coherence tomography (AS-OCT) images of the printed CE lens worn on the cornea upon insertion (middle inset) and after 1 hour of the wear (right inset). FIG. 4D represents full-field ERG signals acquired from the three different devices under the light intensity of 10.0 cd·s·m$^{-2}$. FIG. 4E represents coefficient of variation (CV) of the amplitudes and implicit times of the a- and b-waves extracted from at least 8 recordings.

FIG. 5A shows ISCEV standard full-field ERG signals acquired from the printed CE lens (red lines) by comparisons with those obtained using the ERG-Jet lens (blue lines) and DTL fiber (green lines). FIG. 4B shows a summary of average amplitudes (left column) and implicit times (right column) extracted from each ERG protocol. For data analysis, a one-way analysis of variance (ANOVA) method with Tukey's post hoc test was used. Significance was set at **$p<0.0001$, *$p<0.001$, **$p<0.01$, *$p<0.1$.

FIGS. 6A through 6D schematically represent exemplary procedures for fabricating the printed CE lens. FIGS. 6A through 6C represent a series of computer-controlled automated dispenser-printing processes for the fabrication of the printed CE on a temporary glass substrate coated with a water-soluble PVA layer. The bottom magnified images show the dimensions of each printed layer. FIG. 6D represents an electroplating process of the conduction path (i.e., AgSEBS layer) with Au. The bottom magnified image highlights the change of color to gold after the electroplating process. FIG. 6E represents a transfer printing process of the entire structure from the temporary glass substrate to the inner surface of a SCL. The bottom magnified image highlights the elastomeric connection wire inserted out through the SCL for seamless integration. FIG. 6F represents electrochemical polymerization of EDOT to form a PEDOT layer over the printed CE. The bottom magnified image highlights the monolithic anchoring of the printed CE to the SCL.

DETAILED DESCRIPTION OF THE INVENTION

Figure 1A:
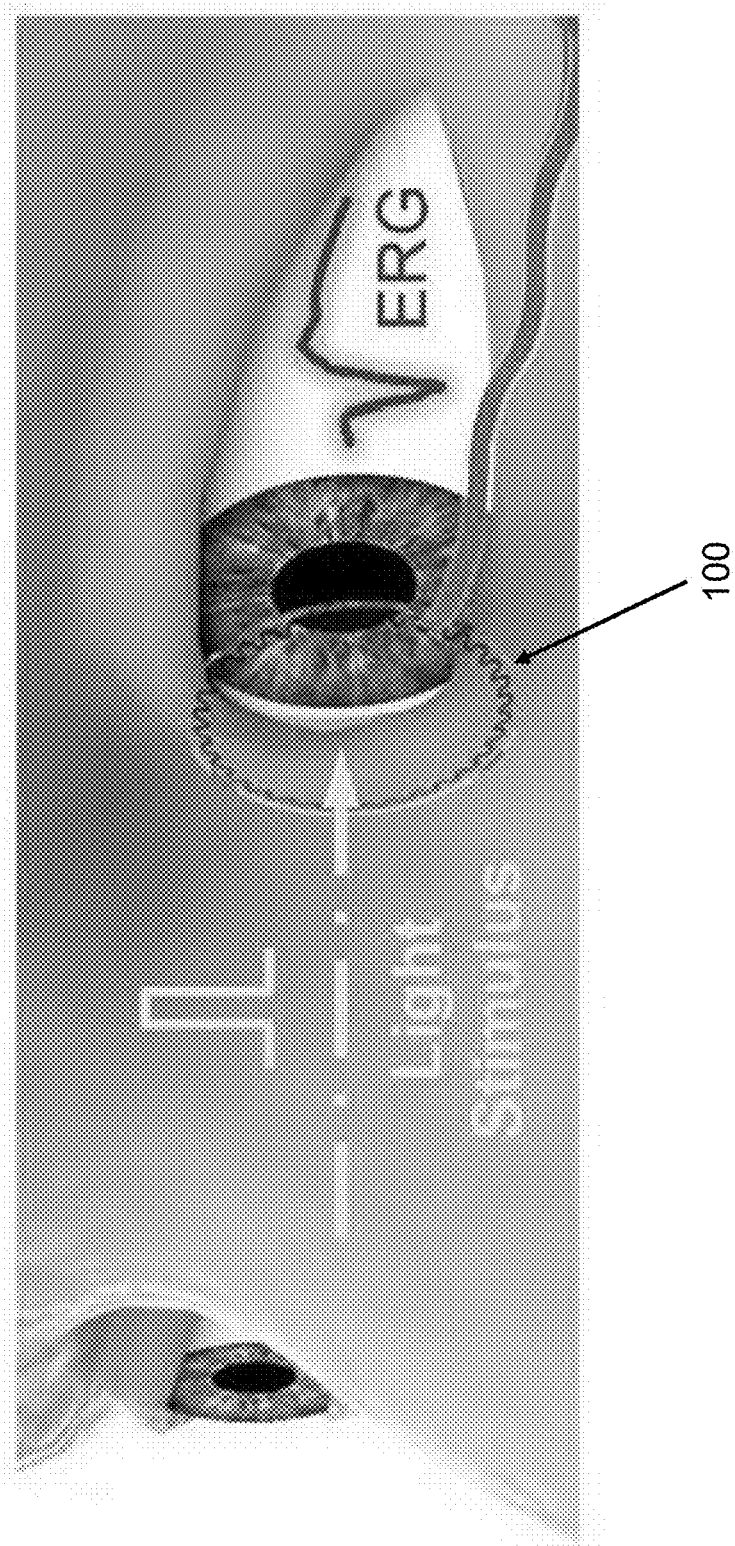
FIGS. 1A through 1E schematically represent and show images of an all-printed stretchable corneal electrode (CE) lens for electroretinogram (ERG) recording in accordance with certain nonlimiting aspects of the invention.

The intended purpose of the following detailed description of the invention and the phraseology and terminology employed therein is to describe what is shown in the drawings, which include the depiction of one or more nonlimiting embodiments of the invention, and to describe certain but not all aspects of what is depicted in the drawings, including the embodiment(s) depicted in the drawings. The following detailed description also describes certain investigations relating to the embodiments depicted in the drawings, and identifies certain but not all alternatives of the embodiment(s) depicted in the drawings. Therefore, the appended claims, and not the detailed description, are intended to particularly point out subject matter regarded as the invention, including certain but not necessarily all of the aspects and alternatives described in the detailed description.

Disclosed herein are eye wearable devices 100 comprising a highly stretchable ERG corneal sensor 102, referred to herein at times as corneal electrodes (CEs), on a disposable soft contact lense (SCLs) 110 (FIG. 1A). The corneal sensor 102 includes a circular serpentine trace of conduction paths 104 located at or near the outer peripheral edge of the SCL 110, allowing light to pass unobstructed through a center region of the SCL 110. Electrochemical deposition and subsequent adhesion of the corneal sensor 102 to the SCL 110 promotes both mechanical robustness against thousands of cycles of folding and scrubbing, as well as chemical stability with lens cleaning and disinfecting solutions. In addition, this approach is applicable to various materials and designs of SCLs 110 that offer excellent biocompatibility, softness (e.g., mechanical modulus (E) of about 0.2 to 2.0 MPa), transparency (about 100%), oxygen permeability (about 10 to 200 Dk/t), wettability (water content of about 30 to 80%), and are able to fit a variety of corneal shapes (e.g., about 8.3 to 9.0 mm base curve radii). The corneal sensor 102 is physically linked to a simultaneously-printed elastomeric connection wire 108 for external connection to a data acquisition system. The connection wire 108 is preferably lightweight (e.g., about 1.4 mg cm$^{-1}$) and highly stretchable (up to 350%) to reduce effects of blinking and eye rotational movements (e.g. on average around ±4 mm) on signal quality. The corneal sensor 102 conforms to the corneal anterior surface as much as the bare SCL 110 does, and provides better comfortability than current clinical standards. These aspects enable the high-fidelity recording of full-field ERG responses in a non-invasive manner without the need of corneal anesthesia or a speculum.

Nonlimiting embodiments of the invention will now be described in reference to experimental investigations leading up to the invention. The results of the human tests demonstrated the feasibility of the printed corneal sensor 102 in a standard ocular electrodiagnostic setting, and from this its suitability for use in SCLs 110 to continuously monitor various physiological parameters that may be used in the diagnosis or detection of diseases, including but not limited to ocular diseases.

Figure 1B:
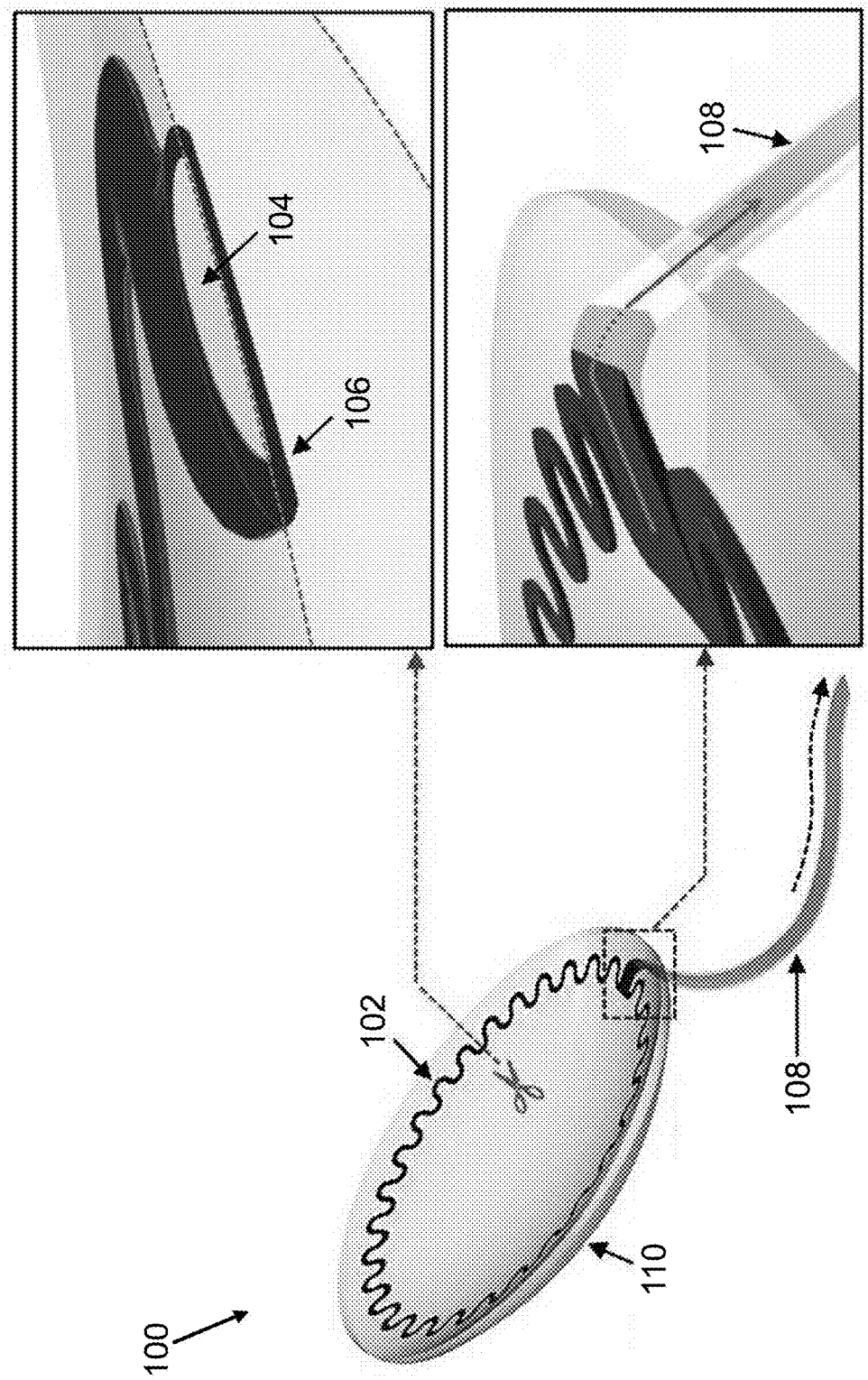
Figure 1C:
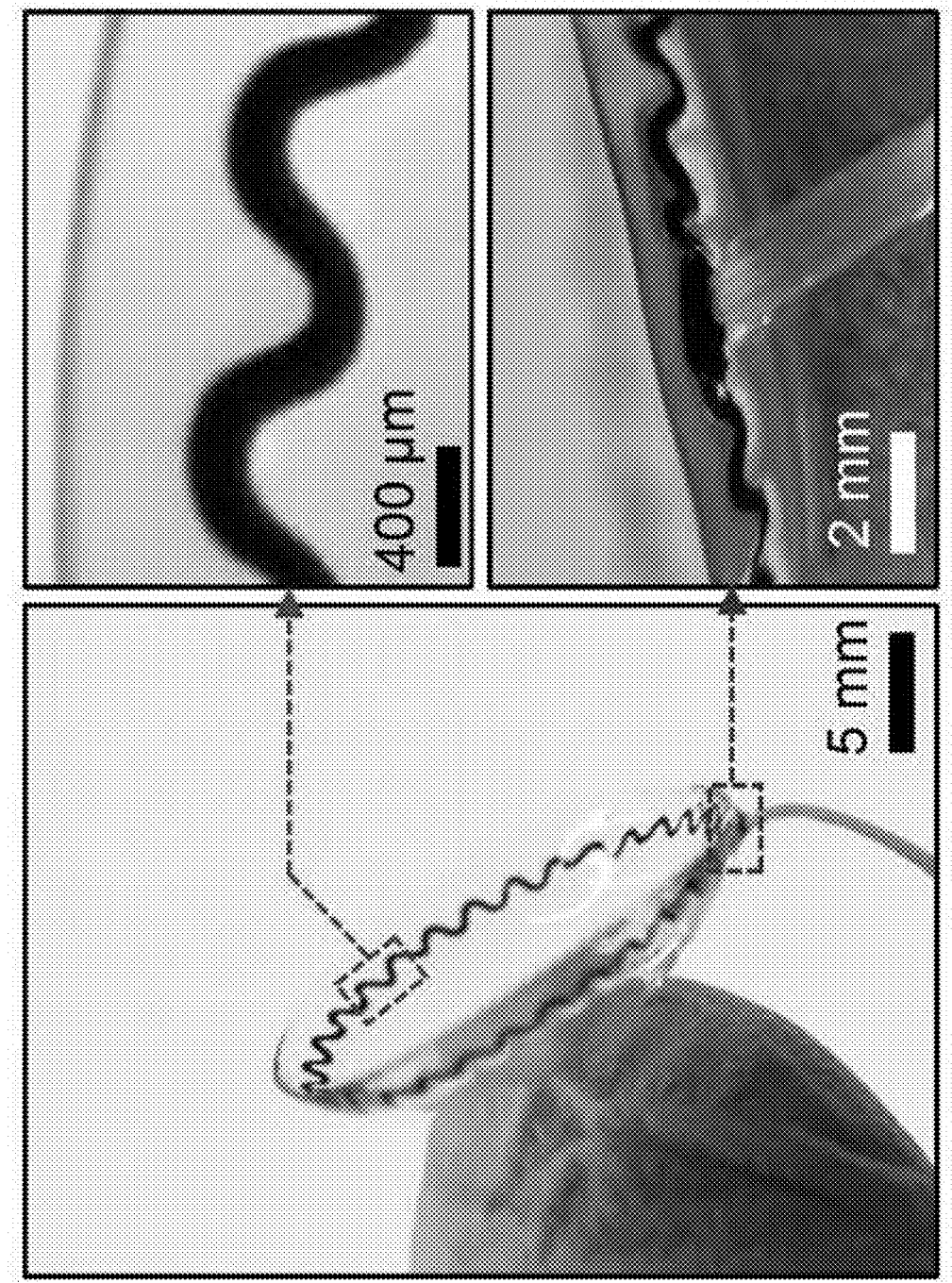

FIG. 1B represents an exemplary nonlimiting embodiment of the device 100. The corneal sensor 102 is configured into a thin, narrow serpentine trace (250 µm-wide×10 µm-thick×66 mm-long) and positioned on the inner surface of the commercially-available disposable SCL 110 facing the corneal surface. A conductive biocompatible polymer, poly(3,4-ethylenedioxythiophene) (PEDOT) doped with tosylate, was electrochemically-printed around the entire outer surface of the corneal sensor 102 in order to provide a thin conduction encapsulation layer 106 and promote anchoring to the SCL 110 (FIG. 1B, top inset image). The corneal sensor 102 was monolithically linked to the elastomeric connection wire 108 (1 mm-wide×120 µm-thick×greater than 5 cm-long) that was comprised custom-formulated elastomers, such as silver flake-filled polystyrene-b-poly(ethylene-co-butylene)-b-polystyrene (AgSEBS) and fumed silica nanoparticle-filled polydimethylsiloxane (PDMS). Here, the connection wire 108 penetrates through the SCL 110 for seamless integration (FIG. 1B, bottom inset image). FIG. 1C shows the overall size and configuration of the corneal sensor 102 built on the disposable SCL 110 (ACUVUE Oasys, Johnson & Johnson; center thickness of 70 µm).

FIGS. 6A through 6F show schematic illustrations of a procedure for fabricating the device 100. The fabrication began with an automated dispenser-printing tool 112 equipped on a three-axis computer-controlled translation stage (Nordson EFD, resolution: 1 µm, repeatability: +/−3 µm). This printing tool 112 allowed for direct-in-writing (DIW) of elastomeric inks (e.g., the formulated AgSEBS and PDMS) on a glass substrate 114 coated with a water-soluble polyvinyl alcohol (PVA) layer 116. This printing technique provided the versatility to write multiple layers of linear and curvilinear traces uniformly at the microscale (greater than 100 µm in width, greater than 10 µm in thickness) in a series of pre-programmed steps, enabling batch production (greater than 10 units per batch).

Figures 6A, 6B, 6C:
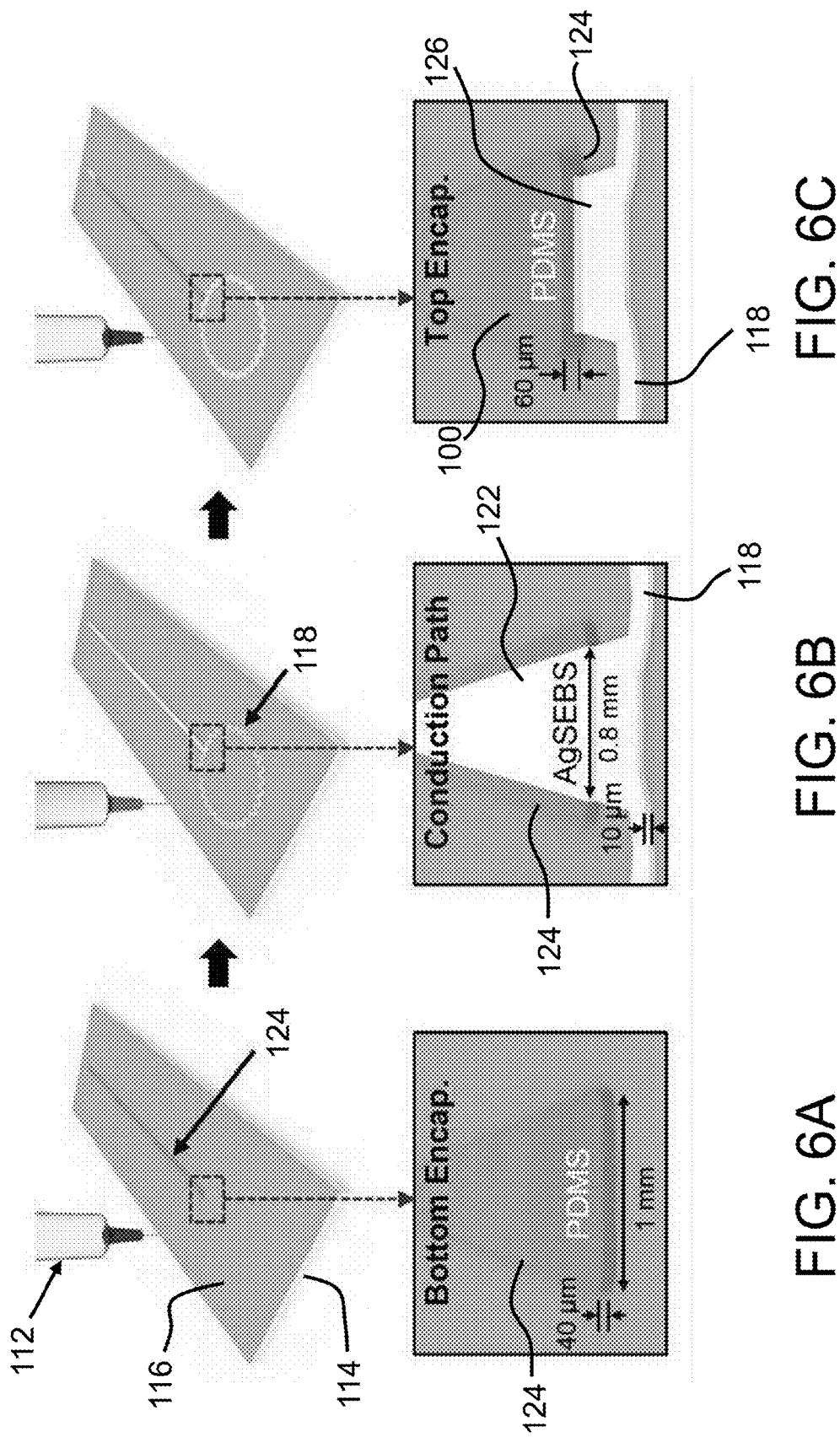

The formulated PDMS ink was prepared by mixing a base solution (DOWSIL SE1700, Sylgard 184, Dow Corning) and curing agent with a weight ratio of 1:1:0.2. The formulated AgSEBS ink was prepared by dissolving 1.5 g of SEBS (H1221, Asahi Kasei) in 1.5 g of tetrahydrofuran (Aldrich) and 4 g of 1,2-dichlorobenzene (Aldrich), and mixing 8 g of Ag flakes (2-5 µm, Inframat Advanced Materials) with a planetary centrifugal mixer (Thinky, ΔRE-310). Direct writing of the PDMS ink was carried out on the glass substrate 114 coated with the PVA sacrificial layer 116 to define a bottom insulation encapsulation layer 124 of the connection wire 108 (FIG. 6A). Following thermal annealing of the printed PDMS ink at 70° C. for 30 minutes, another direct writing of the AgSEBS ink was carried out to define an inner conduction path 118 of the sensor 102 and a conduction path 122 of the connection wire 108 (FIG. 6B). The entire structure was then heated at 70° C. for 1 hour. Finally, one more direct writing of the PDMS ink was carried out to define a top insulation encapsulation layer 126 of the connection wire 108 (FIG. 6C), followed by annealing at 70° C. for 30 minutes.

The next step involved removing the water-soluble PVA layer 116 with deionized (DI) water, followed by electroplating the inner conduction path 118 (i.e., AgSEBS) with gold (Au) to define an outer conduction path 120 not only to promote electrical conductivity but also to enhance scratch resistance and chemical stability within aqueous media (FIG. 6D).

Figure 7:
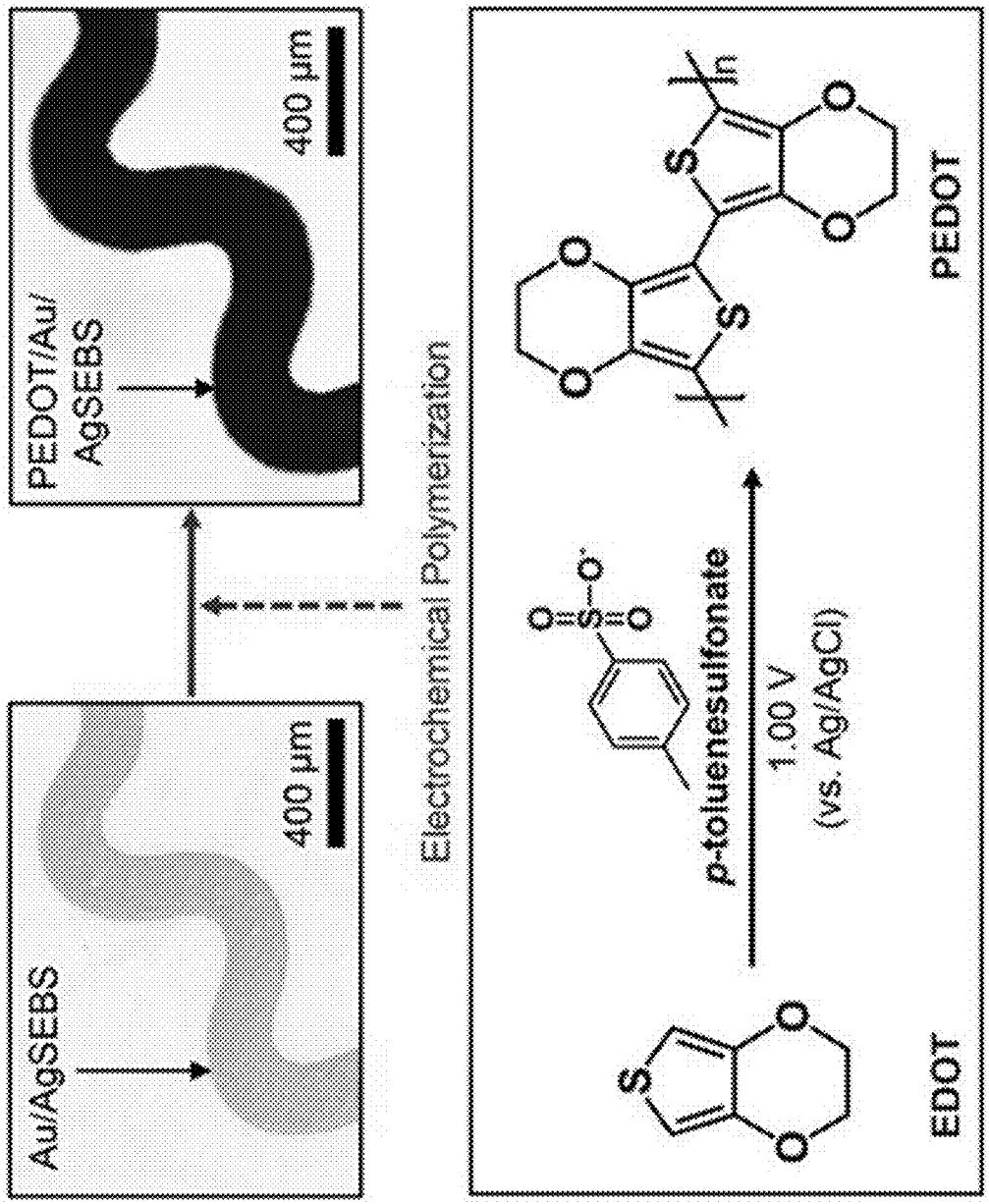
FIG. 7 represents electrochemical polymerization of PEDOT. Enlarged microscope images of the printed CE before (top left image) and after (top right image) the electrochemical polymerization of PEDOT are provided, with a scheme of the electrochemical polymerization process (bottom image).

The corneal sensor 102 was then transferred to the inner surface of the SCL 110 under a microscope, while the elastomeric connection wire 108 was inserted out through the SCL 110 (FIG. 6E). The serpentine trace of the corneal sensor 102 was stretched when contacted to the curvilinear surface of the SCL 110 until it accommodated the interfacial stress, thereby avoiding any surface discontinuity. The next step involved an electrochemical polymerization of 3,4-ethylenedioxythiophene (EDOT) to form a thin PEDOT layer over the Au-coated surface (FIGS. 6F and 7) to define the conduction encapsulation layer 106. The bonding process began by immersing the SCL 110 in an electrolyte solution containing $50 \times 10^{-3}$ M EDOT monomer and $100 \times 10^{-3}$ M LiClO$_4$ dopant and keeping it overnight at 4° C. to exchange the lens solution with the electrolyte solution. The pre-prepared sensor 102 was then placed on the surface of the monomer-containing SCL 110. Here, the sensor 102 can be located in the peripheral area of the SCL 110 in a circular path, thereby minimally impacting on the vision, light, oxygen permeability, and flexibility on the scl 110. Subsequently, an electrochemical potential of 1.0V versus Ag/AgCl to the conductive path 104 was applied, allowing the EDOT to be polymerized into PEDOT at the interface. Finally, the resulting device 100 was thoroughly washed with a preservative-free saline solution, followed by an overnight sterilization process with a commercial disinfection hydrogen peroxide ($H_2O_2$) solution.

Figure 1D:
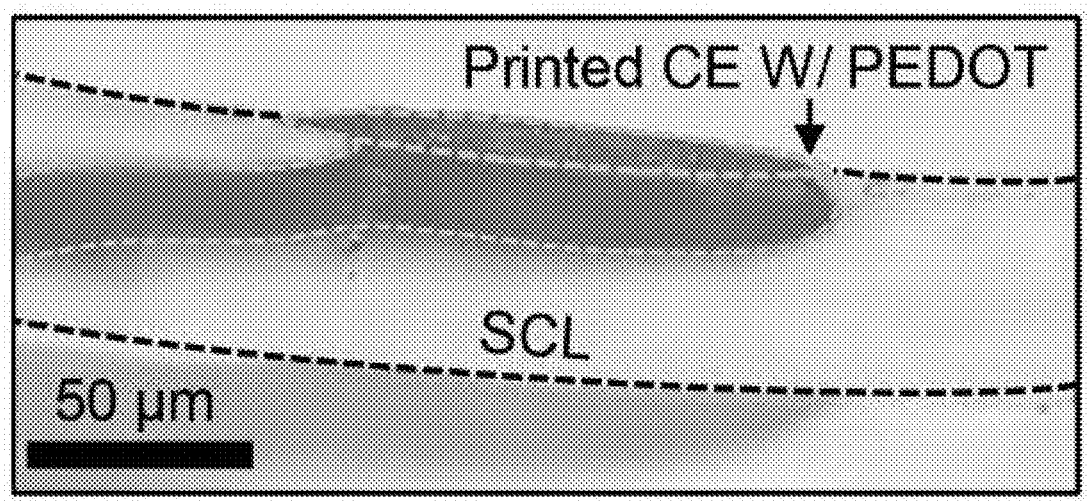
Figure 1E:
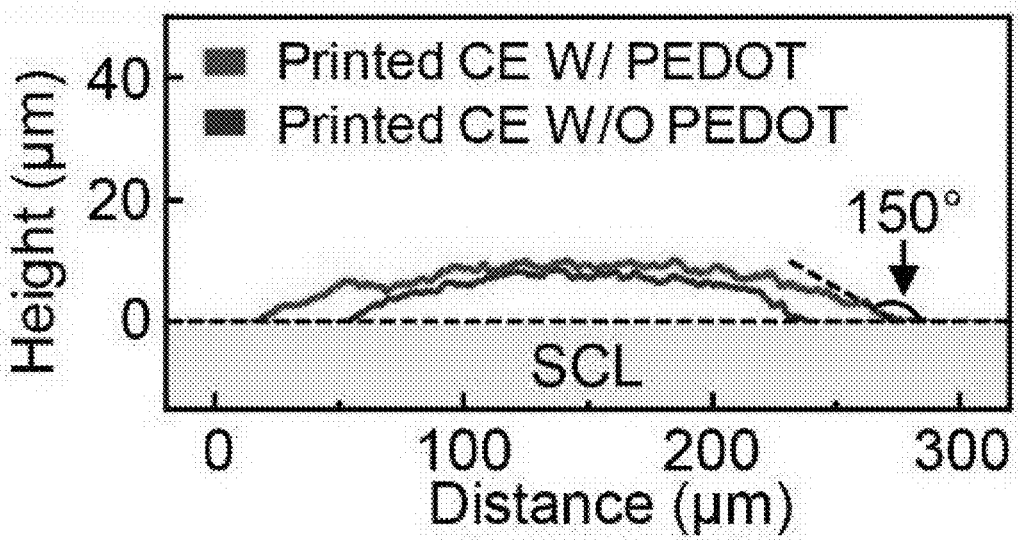

The cross-sectional microscope image in FIG. 1D shows that the electrochemically grown PEDOT layer (conduction encapsulation layer 106) conformed to the surface of the corneal sensor 102 and seamlessly penetrated the SCL 110. FIG. 1E shows the surface topology of the corneal sensor 102 with (red line) and without (blue line) a PEDOT layer, of which the electrochemical processing time was fixed at 4 minutes. The results indicate that the peak heights remained below 10 μm, while the formation of the PEDOT layer occurred predominantly at the edge of the corneal sensor 102 due to uneven current distribution across the round surface. Consequently, a gradual taper angle of less than or equal to 30° was created at the edge of the PEDOT layer, offering enhanced conformal contact to the corneal surface. These features promote minimization of irritation to the cornea, while reducing the edge stress. These observations were reproducible across different types (e.g., materials, water content, and ionicity) of commercially-available disposable SCLs 110.

Figures 2A, 2B, 2C:
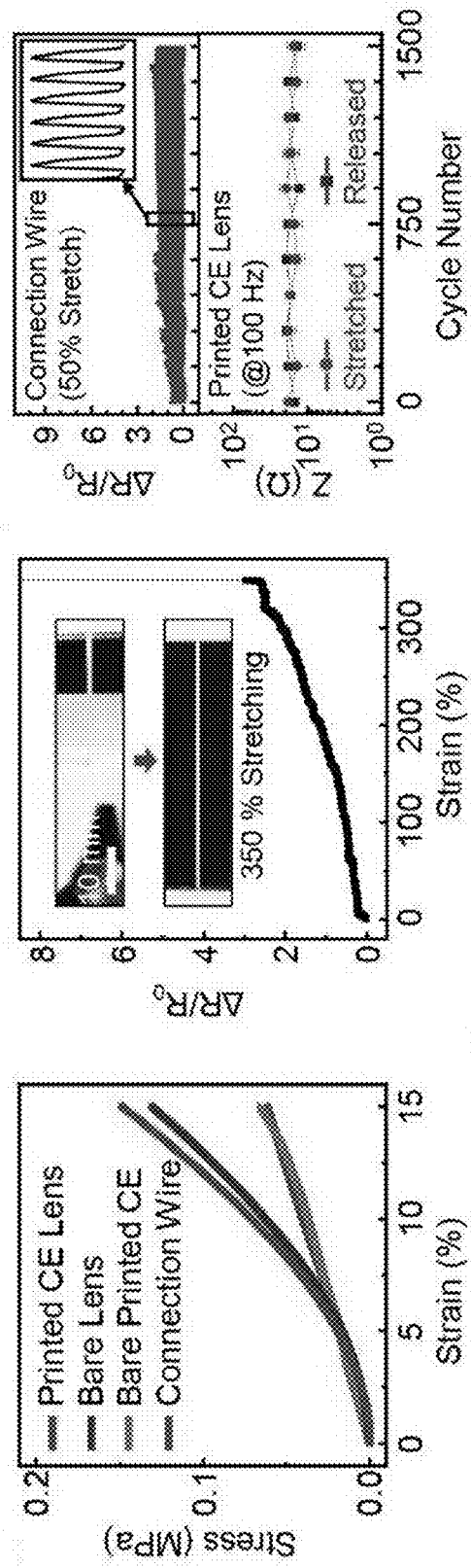
FIGS. 2A through 2B represents characterizations of the all-printed stretchable CE lens.
FIG. 2C shows $\Delta R/R_0$ of the elastomeric connection wire under 1,500 cycles of stretching at 50% (top panel) and the consequent change in the electrochemical impedance of the printed CE lens at every 150 cycles (bottom panel).
Figures 2D, 2E, 2F:
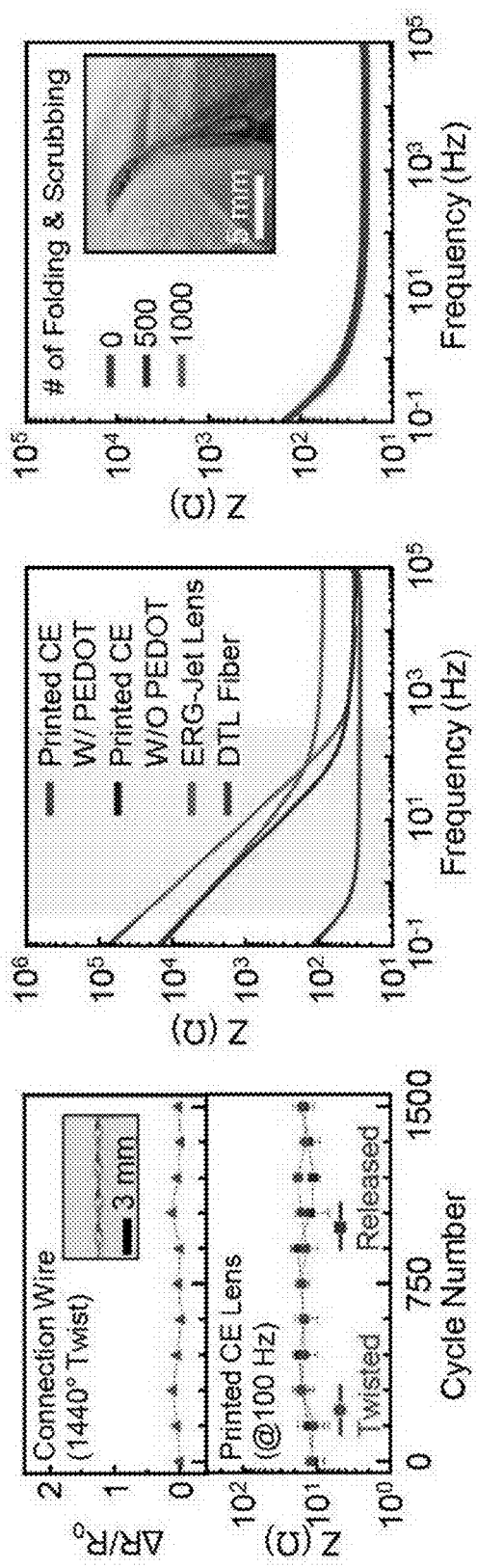
FIG. 2D shows $\Delta R/R_0$ of the elastomeric connection wire under 1,500 cycles of twisting up to 1,440° (top panel) and the consequent change in the electrochemical impedance of the printed CE lens at every 150 cycles (bottom panel).
FIG. 2E shows electrochemical impedance of the printed CE lens as a function of frequency by comparisons with current clinical standards.
FIG. 2F shows electrochemical impedance of the printed CE lens under 1,000 cycles of folding and scrubbing.
Figure 8:
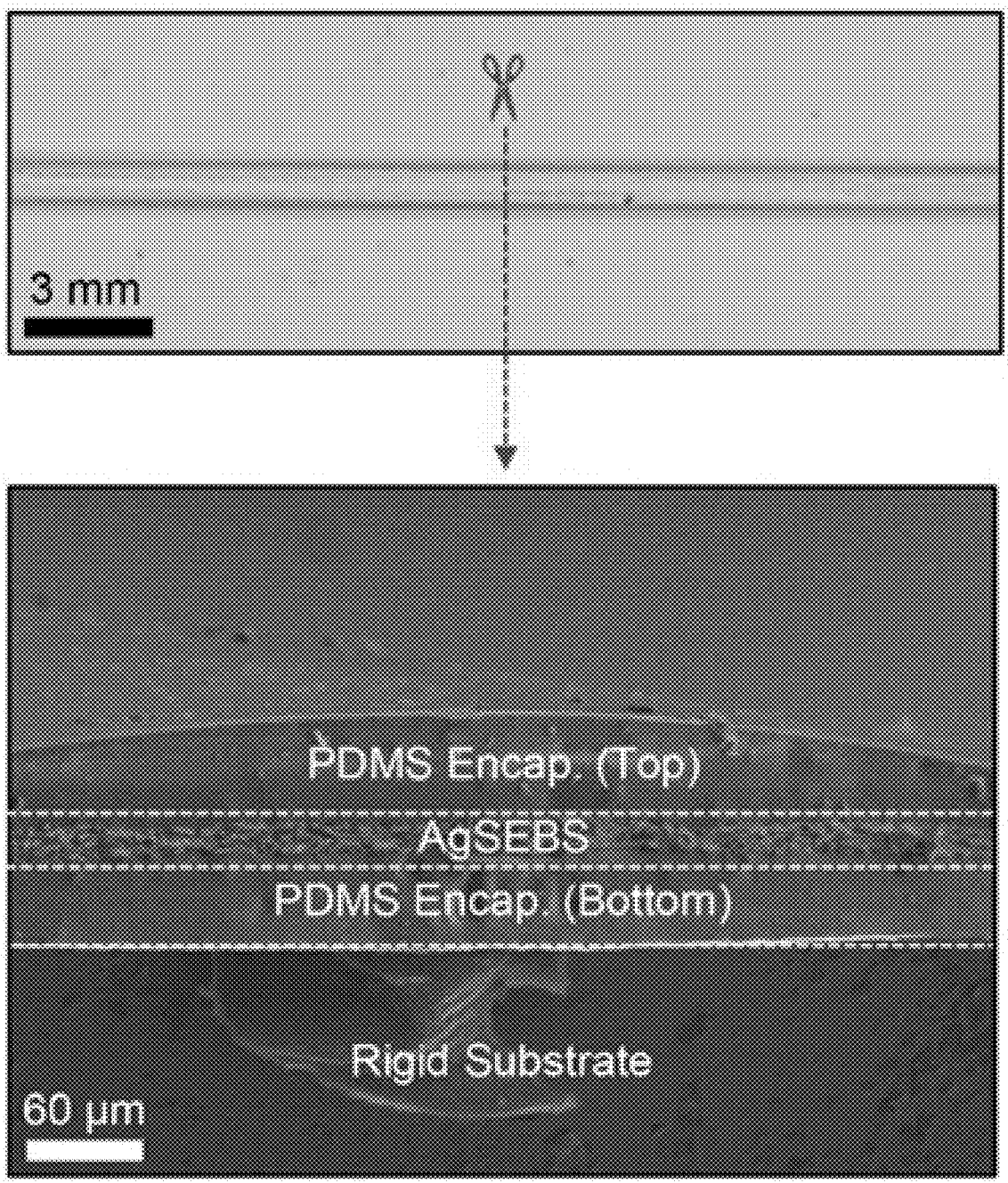
FIG. 8 represents an exemplary layout of the elastomeric connection wire. Top-view photograph (top inset) and cross-sectional scanning electron microscope (SEM) image (bottom inset) of the printed elastomeric connection wire.

The experimental results represented in FIG. 2A show that the device 100 provided a similar modulus (E=790±140 kPa) to the bare control SCL 110 (blue line; ACUVUE Oasys, Johnson & Johnson), while the corneal sensor 102 without the SCL 110 provides greater than two times lower modulus (green line; E=374±47 kPa). The intrinsically low modulus of the bare corneal sensor 102 allows its addition to the SCL 110 without substantially altering the mechanical properties of the SCL 110, which would otherwise perform differently. In fact, the bare corneal sensor 102 was at least seven times thinner than the SCL 110 (greater than 70 μm-thick) and covered only 8% of the total surface area of the SCL 110 on the peripheral edge to further minimize the effect on overall lens performance. For example, the corneal sensor 102 was stretched without failure even after the SCL 110 was torn into two pieces at the maximum strain of about 100%. The results also show that the monolithically integrated elastomeric connection wire 108 (purple line; E=420±41 kPa) was virtually as soft as the bare corneal sensor 102, and therefore should have minimal effect on blinking or eye movements. The connection wire 108 was stretched up to 350% prior to its mechanical failure, while the relative change in resistance ($\Delta R/R_0$) remained below 2.7 (FIG. 2B). A representative cross-sectional scanning electron microscope (SEM) image of the connection wire 108 is shown in FIG. 8. The mechanical and electrical properties of the connection wire 108 were negligibly changed after greater than 1,500 cycles of stretching at 50% (FIG. 2C, top panel), resulting in well-maintained electrochemical impedance of the corneal sensor 102 (FIG. 2C, bottom panel). These assessments were consistent with the experimental observations by twisting the connection wire 108 up to 1,440° for more than 1,500 cycles (FIG. 2D). In addition, its electrochemical impedance remained sufficiently low at about 18.2±3.8 ohms even against tapping, swinging, and spinning of the connection wire, implying that the effect of motion artifacts (e.g., blinking or eye movement) on signal quality was insignificant.

Figures 2G, 2H, 2I:
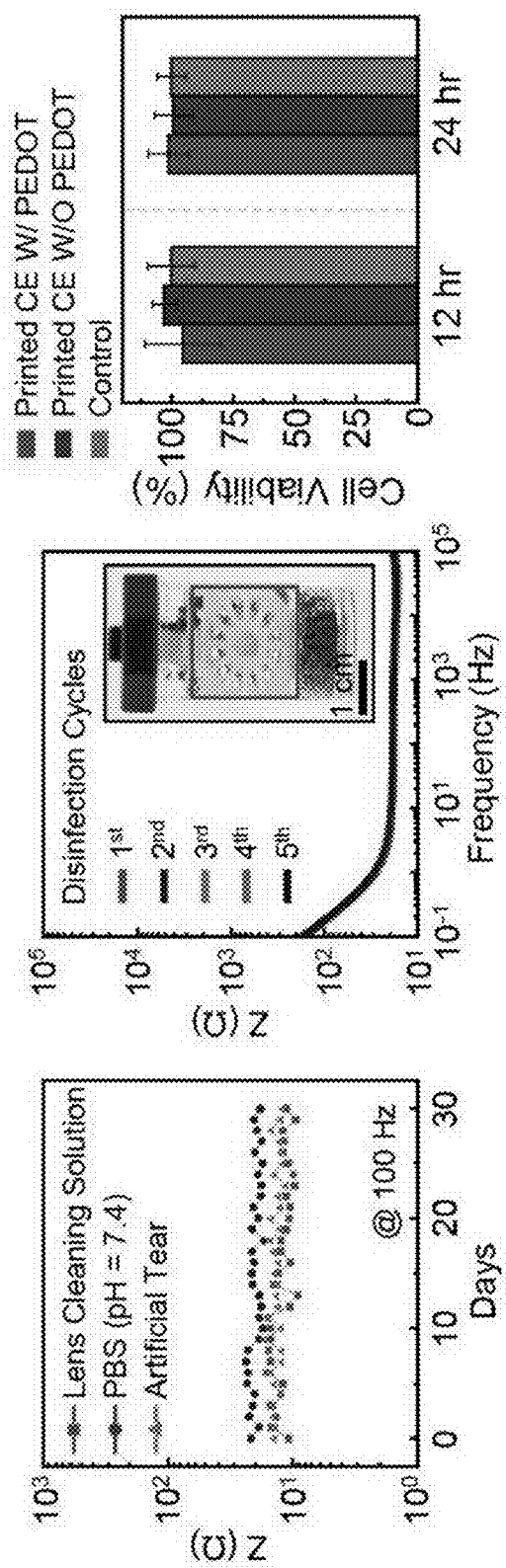
FIG. 2G shows electrochemical impedance of the printed CE lens immersing in several aqueous media for 30 days.
FIG. 2H shows electrochemical impedance of the printed CE lens for 5 cycles of disinfection processes. The inset image shows a commercial cleansing kit filled with a 3% $H_2O_2$ formula.
FIG. 2I shows cell viability assay of human corneal epithelial cells (HCEpiC) seeded on the printed CE lens with and without a PEDOT layer by comparison with bare control cells.

FIG. 2E shows experimental measurements for the frequency-dependent electrochemical impedance of the corneal sensor 102 with (red line) and without (blue line) a PEDOT layer in a solution of 1× phosphate-buffered saline (PBS, pH=7.4), by comparison with commonly used clinical standards such as the ERG-Jet lens (LKC Technologies; center lens thickness of 500 μm) and the DTL fiber (Diagnosys; seven times interwoven fiber with the outer diameter of 0.8 mm). The corneal sensor 102 with a PEDOT layer 106 showed the lowest impedance (less than 100Ω) among the three devices within the typical frequency range of ERG recordings in human eyes (gray highlighted area; 0.3 to 300 Hz), which would therefore give rise to high signal-to-noise ratio. These observations were reproducible from device to device. The impedance of the corneal sensor 102 was nearly unchanged over greater than 1,000 cycles of folding and scrubbing (FIG. 2F) and after 30 days of immersion in several aqueous media, such as lens cleaning solution (Sensitive Eyes® saline solution, Bausch & Lomb), PBS (pH=7.4; Gibco), and artificial tear (Refresh Tears® lubricant eye drops, Allergan) at 100 Hz (FIG. 2G). FIG. 2H confirms that the impedance was negligibly changed throughout the multiple disinfection cycles (greater than 5 times) by immersing the corneal sensor 102 in a cleansing kit (inset image) filled with a 3% $H_2O_2$ formula (ClearCare®, Alcon) for 12 hours each. During these disinfection cycles, no evidence of visual changes in the appearance of the corneal sensor 102 was observed. The impedance was also well maintained under other harsh environmental conditions, such as temperature cycling between 30 and 80° C. and multiple dehydrations in ambient conditions for at least five hours each. The impedance was slightly decreased at a high temperature (e.g., greater than about 60° C.).

Time-dependent cytotoxicity of the corneal sensor 102 to human corneal cell lines is an important consideration to identify any adverse responses in vitro. FIG. 2I shows a cell viability assay of human corneal epithelial cells (HCEpiC) that were seeded on the surface of the corneal sensor 102 with (red bars) and without (blue bars) a PEDOT layer in a culture medium (EpiGRO™ Human Ocular Epithelia Complete Media, MilliporeSigma) at 37.5° C. For all cases, the cell viabilities were retained over 95% throughout the entire assay period (24 hours) without substantial differences relative to bare control cells (green bars). The results imply that the corneal sensor 102 would provide little risk for the development of corneal inflammation during ERG examinations. The results also confirm that there was no residual EDOT present after the washing and disinfecting processes.

Figure 3A:
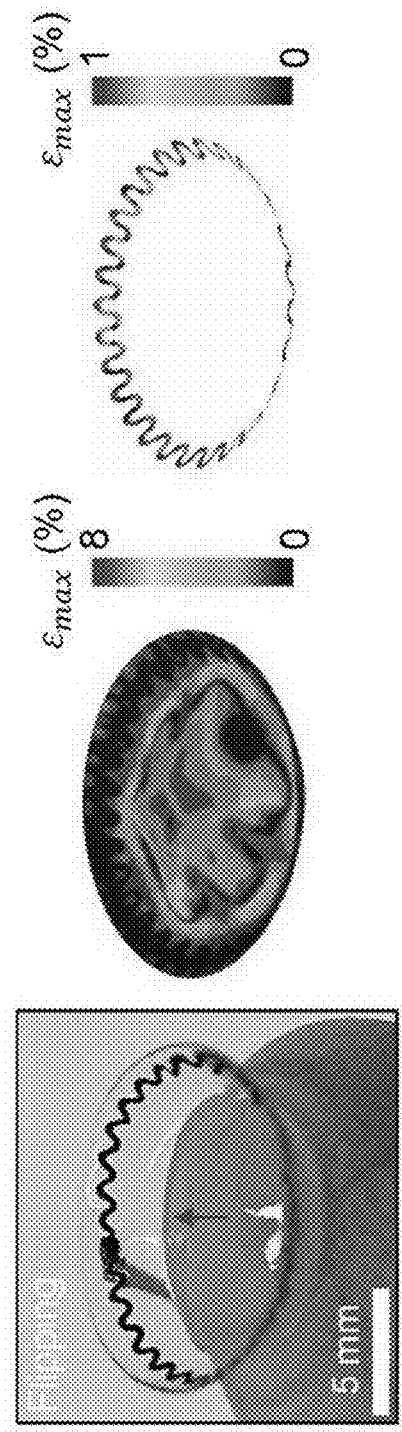
FIGS. 3A through 3D represent mechanics analysis under various loading conditions. Photographs (left column) and finite element analysis (FEA) results (middle column) of the printed CE lens under 4 different loading conditions.
Figure 3B:
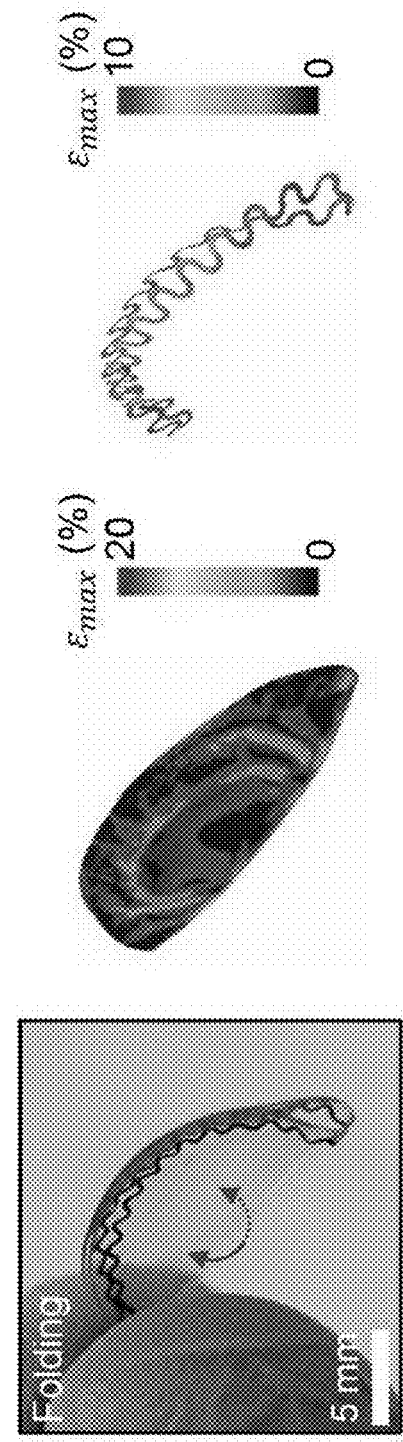
Figure 3C:
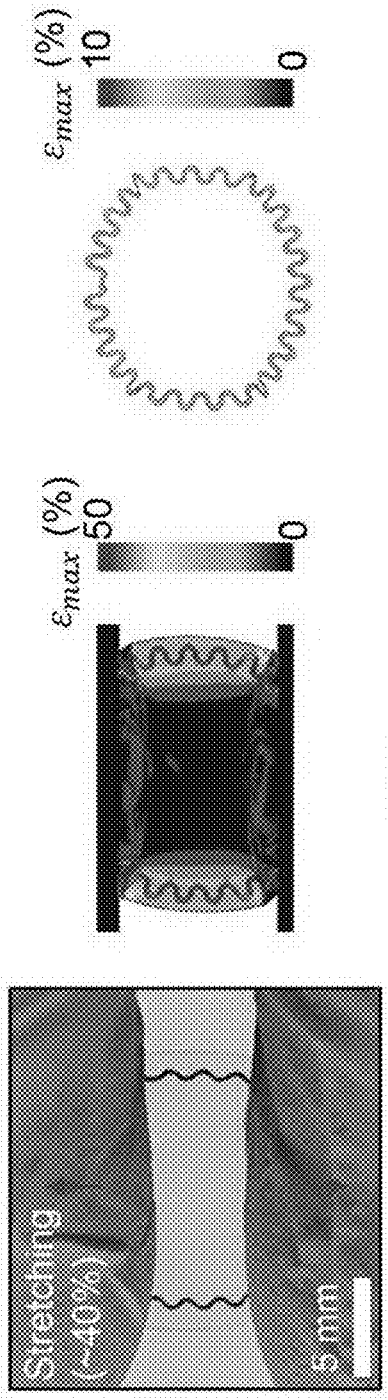
Figure 3D:
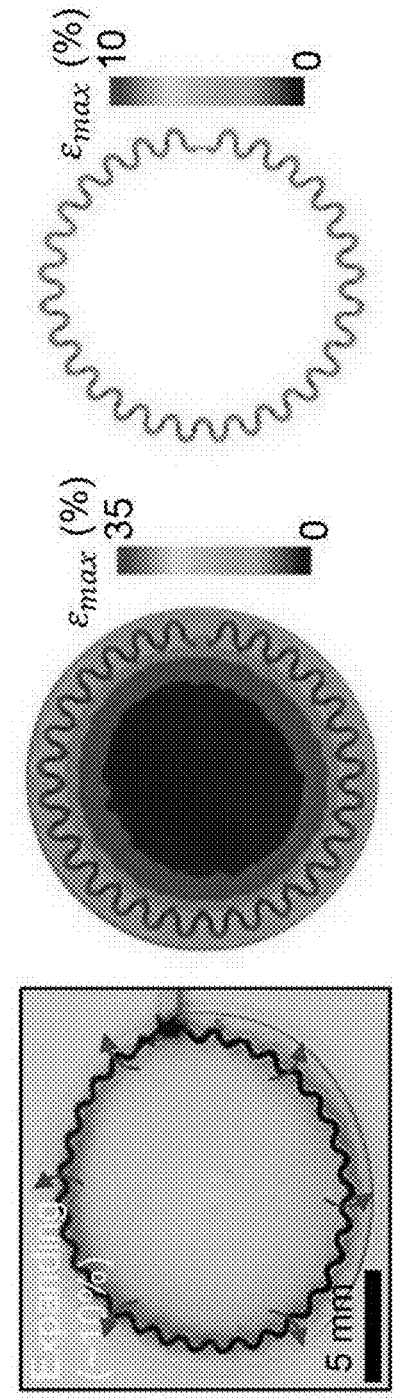

The low mechanical modulus of the corneal sensor 102 reduces the risk for mechanical failure against various loading conditions required for lens handling, cleaning, storage, and fitting. FIGS. 3A through 3D summarize experimental (left column) and finite element analysis (FEA; middle column) results of the device 100 under 4 different loading conditions: (FIG. 3A) flipping, (FIG. 3B) folding, (FIG. 3C) stretching (up to 40%), and (FIG. 3D) expanding (up to 10%). For control comparisons, the corresponding FEA results for the bare corneal sensor 102 without the SCL 110 are shown in the right columns of FIGS. 3A through 3D. The results show that the maximum principle strain ($\varepsilon_{max}$) of the corneal sensor 102 remained lower than about 10% under these loading conditions. For example, when completely flipped over, the corneal sensor 102 experienced little deformation with the maximum strain of less than 1% (FIG. 3A). When folded in half along the symmetric axis, the maximum strain (less than 10%) was concentrated at the folding line of the corneal sensor 102 (FIG. 3B). When stretched uniaxially and expanded uniformly, the results consistently showed the maximum strain remained less than 10% (FIGS. 3C and 3D). For all cases, the maximum strains of the corneal sensor 102 were higher than those of the bare corneal sensor 102 (without the SCL 100) by several factors, indicating that the mechanical deformations occurred primarily on the SCL 110 rather than the corneal sensor 102. These findings also imply that the effect of the bare corneal sensor 102 on the intrinsic mechanical properties of the SCL 110 was insignificant.

Figures 4A, 4B:
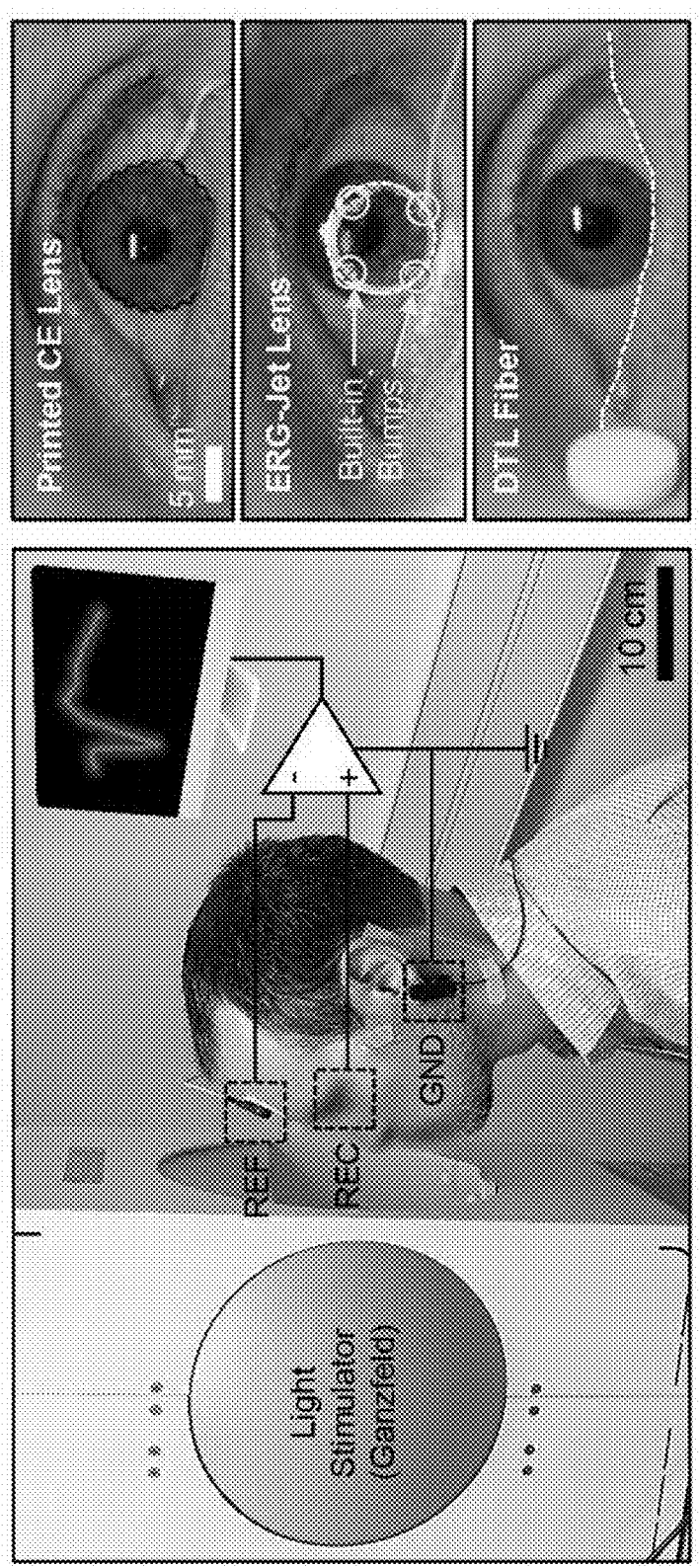

To demonstrate the feasibility and measurement validity in the human eye, an evaluation of the device 100 was conducted by clinical research-trained personnel on a healthy adult participant (a 45-year-old male) who had no history of ocular disease. Prior to and following ERG recordings, several pre-examination data were acquired including visual acuity, participant-reported comfort ratings, ocular coherence tomography (OCT; Visante, Zeiss), and slit lamp biomicroscopic (SL120, Zeiss) measures of ocular health and lens fit. The slit lamp biomicroscopic measures were acquired with normal white lights as well as sodium fluorescein installation (1 mg; Fluorets ophthalmic strips, Bausch and Lomb) which highlights any area of damage on the corneal epithelial surface. The ERG recordings were acquired with the device 100 and two comparator controls; the ERG-Jet lens and DTL fiber. The Burian-Allen ERG electrode was not included in this experiment due to its high discomfort and low tolerance experienced by the participant FIG. 4A demonstrates the process of ERG recordings where the participant was seated upright in front of a Ganzfeld stimulator (RETI-port/scan 21, Roland Consult), which generated a series of short-wavelength stimuli in low luminance conditions (about 0.001 cd m$^{-2}$). The device 100 was inserted on the left eye of the participant without topical anesthesia or a speculum, and the participant was asked to blink normally. Biomicroscopic examination revealed a mobile, well-fit lens with good centration, coverage, and movement (FIG. 4B, top panel). Both the corneal sensor 102 and the connection wire 108 had little impact on blinking or eye movements with the gaze angle of up to ±40° (which most commonly occur), resulting in the lens movements being as smooth as the bare SCL 110. In a temporal gaze larger than these angles (which is not common in normal eye movements), the connection wire 108 temporarily adhered to the wet conjunctival epithelium and prevented the SCL 110 from continuing to rotate with the eye. This impact could be minimized by the selective inferior placement of the connection wire 108. For control comparisons, both the ERG-Jet lens and DTL fiber were tested on the same eye of the participant to maximize comparison of the techniques and eliminate the effect of different eye sizes and shape on the ERG signals (FIG. 4B, middle and bottom panels, respectively). Moreover, the ERG signals were independent of the size and shape of the human eye, and thereby the ERG measurement required no calibration among different subjects because initial participant measurement data were used as a reference baseline. Prior to the implementation of the ERG-Jet lens, the eye was anesthetized with one drop of 0.5% proparacaine hydrochloride and then moistened with 0.5% methylcellulose in order to reduce discomfort. No speculum was used, but the participant was not able to fully blink with the lens in due to the four built-in anterior bumps (yellow circles; 1.5 mm wide and 2.5 mm long each) preventing complete eyelid closure. The base curve radius of the lens was 7.9 mm, which is slightly flat relative to the central corneal curvature of the participant (7.7 mm). Care was taken to ensure adequate alignment of the lens over the pupil center during measurements, but as is typical for any rigid lens, it moved around 1 to 1.5 mm on the eye. As the last control measure, the DTL fiber was gently placed across the bulbar conjunctiva above the lower eyelid without topical anesthesia.

FIG. 4C shows representative images of anterior segment ocular coherence tomography (AS-OCT), confirming the conformational alignment of the device 100 with the cornea upon insertion (middle inset) and after one hour of wear (right inset). The corresponding AS-OCT images using the ERG-Jet lens could not be acquired due to the unstable contact of the device to the anterior corneal surface and the built-in bumps preventing axial instrument focus. Participant-reported comfort was assessed prior to and during each use of the devices employing a simple 100-point numeric scale, where a rating of "1" represented extremely uncomfortable/intolerable and a rating of "100" perfectly comfortable/not noticeable at all. Prior to testing, the participant provided a rating of "95" with his habitual SCLs (Dailies Aqua Comfort Plus, Alcon), compared to a rating of "98" with no contact lens at all. The DTL fiber was given a rating of "88" versus the device 100 of "86" (both without topical anesthesia). Alternatively, the ERG-Jet lens with topical anesthesia was given a numeric rating of "42."

These tests revealed the following important findings: (1) The device 100 conformed well to the cornea when on the eye, whereas the ERG-Jet lens created a gap between the corneal sensor and cornea of about 500 µm (the sum of the lens thickness and a thick aqueous tear layer between the posterior lens and anterior cornea) due to its relatively flat curvature. (2) The device 100 remained centered on the cornea, whereas the ERG-Jet lens was systematically decentered. (3) The device 100 was rated to be much more comfortable and easier to use than the ERG-Jet lens even without the use of topical anesthesia, and in line with the DTL fiber that was not in contact with the cornea. (4) The external connection wire 108 of these device 100 thin (120 µm thick), lightweight (about 1.4 mg cm$^{-1}$), and sufficiently soft (E=420 kPA) enough to avoid any interruption from blinking and eye movements. On the other hand, the polyvinyl chloride (PVC)-coated lead cable of the ERG-Jet lens was considerably thick (0.6 mm diameter), heavy (8.6 mg cm$^{-1}$), and stiff (E=1.3 GPa), making it difficult to align the lens to the pupil center and capture consistent ERG signals. These experimental observations obtained with the ERG-Jet lens and the DTL fiber were consistent with previous reports.

Following application of the devices and prior to ERG recording, the participant was asked to sit in the low luminance room (less than 0.001 cd m$^{-2}$) for at least 20 minutes. The participant was then asked to gaze at a fixation spot inside the Ganzfeld bowl to maintain a constant amount of light transmission to the retina and minimize interference that could be generated upon ocular movements. The participant's head was kept within 5 cm from the Ganzfeld bowl opening. The pupil size was continuously monitored using an infrared (IR) camera inside the Ganzfeld dome. FIG. 4D shows representative ERG signals obtained by consecutively illuminating a white flashing stimulus (10.0 cd·s m$^{-2}$) for 2 ms at the interval of 20 s to allow the pupil to fully dilate again. For all devices, the results showed typical scotopic ERG waveforms with characteristic a wave (i.e., the first negative wave reflecting the function of photoreceptor) and b wave (i.e., the following positive wave reflecting the activity of rod bipolar cells). The corresponding coefficient of variation (CV) of the amplitudes and implicit times of the ERG waveforms is summarized in FIG. 4E. It is clear that the device 100 provided the highest signal amplitude of the a and b waves, while the measurements were most consistent (CV of less than 6.4%) without noticeable blinking artifacts. These results suggest that the device 100 more intimately interfaced with the corneal surface than other devices, despite blinking and eye movements. The ERG-Jet lens also exhibited high signal amplitude, but the measurements were unstable (CV greater than 15.7% in amplitudes) due to the non-conformal contact to the eye. In addition, the required use of corneal anesthetic agents for the ERG-Jet lens might provide a potential risk of reducing the amplitudes and prolonging the implicit times. As expected, the DTL fiber showed the lowest amplitude signals due to the far distance from the cornea, and the measurements were prone to variations by blinking artifacts (CV of greater than 10% in amplitudes).

The visual acuity of the participant (20/15) remained unchanged prior to and following testing with each of the devices. Upon slit lamp biomicroscopic examination with sodium fluorescein installation prior to testing, the participant had only minor, nonclinically significant superficial punctate staining (common to minor end of day dryness with soft lens wear). Following wear of the device 100 greater than one hour, the punctate staining had resolved. However, a nonclinically significant minor indentation arcuate staining (about 1 mm in extent) was present in one quadrant of the superior cornea, which mirrored the location and orientation of the serpentine trace of the corneal sensor 102. This staining resolved within two hours post lens removal.

Figure 9:
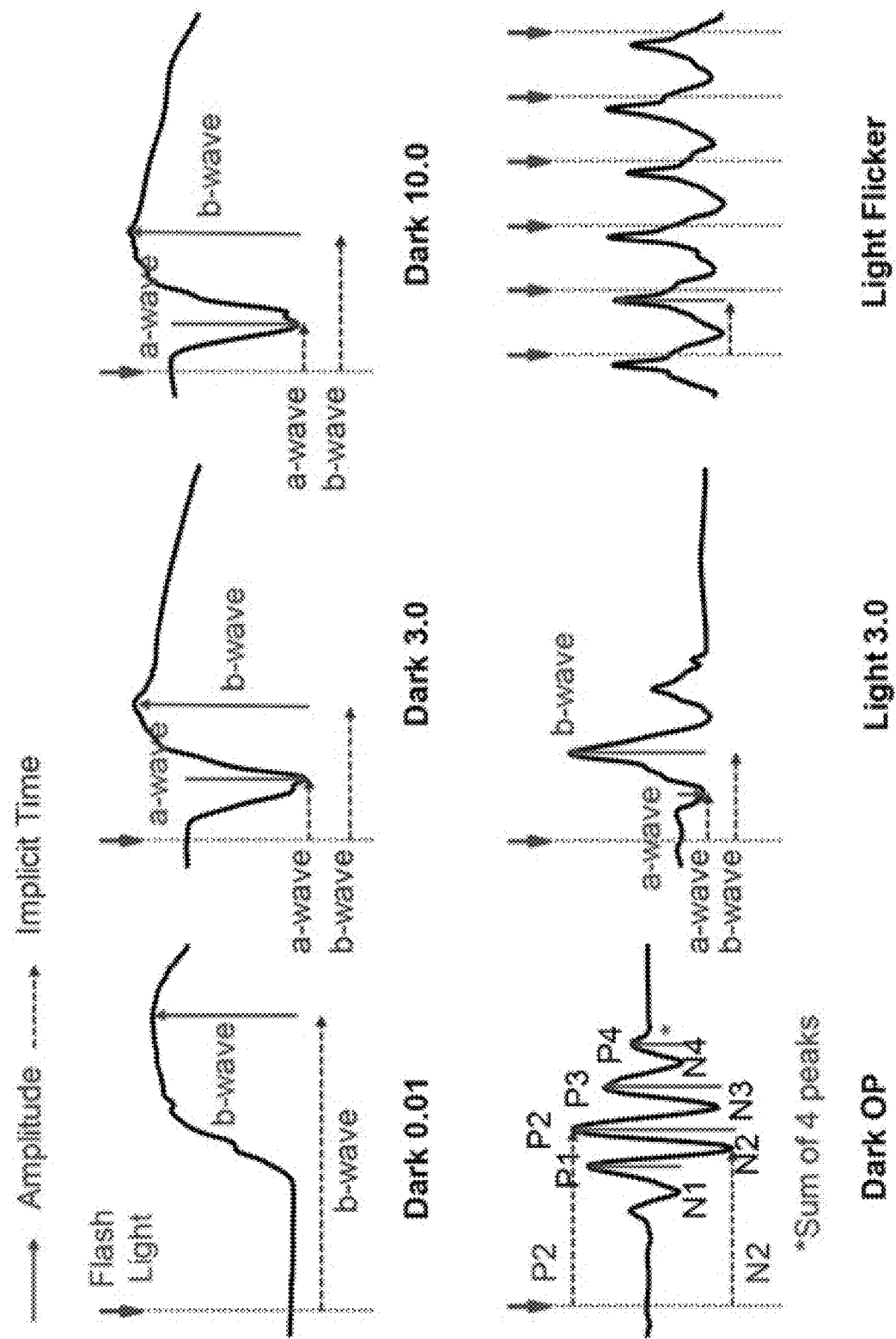
FIG. 9 represents ISCEV standard full-field ERG signals. The amplitudes (red lines) and implicit times (blue lines) of the a- and b-waves obtained from each ERG protocol are noted. Purple dotted lines indicate the moment of flashing light. In case of the Dark OP, the amplitude is considered as the sum of the 4 red arrows.

The International Society for Clinical Electrophysiology of Vision (ISCEV) standard for full-field clinical ERG signals specifies six responses based on the adaptation state of human eyes and the flash strength: (1) Dark-adapted 0.01 ERG (rod ERG), (2) Dark-adapted 3.0 ERG (combined rod-cone standard flash ERG), (3) Dark-adapted 3.0 oscillatory potentials, (4) Dark-adapted 10.0 ERG (strong flash ERG), (5) Light-adapted 3.0 ERG (standard flash "cone" ERG), and (6) Light-adapted 30 Hz flicker ERG37. The ISCEV encourages the use of additional ERG protocols for testing beyond the minimum standard for clinical ERG signals, which are abbreviated as Dark 0.01, Dark 3.0, Dark OP, Dark 10.0, Light 3.0, and Light flicker, respectively. The standard ERG waveforms with characteristic amplitudes and implicit times are noted in FIG. 9.

Figure 5A:
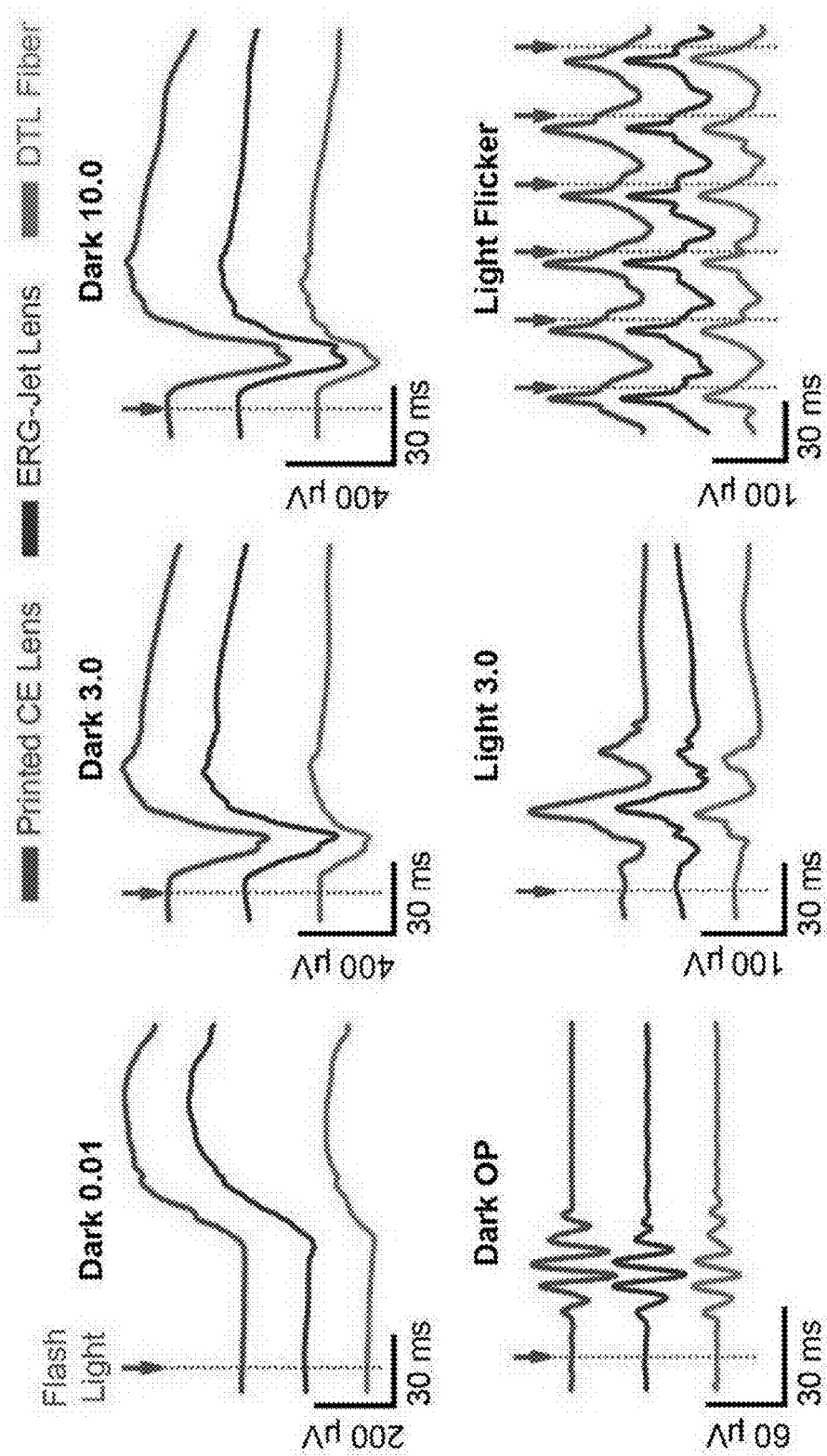
FIGS. 5A and 5B represent ISCEV standard full-field ERG recordings in a human eye.
Figure 5B:
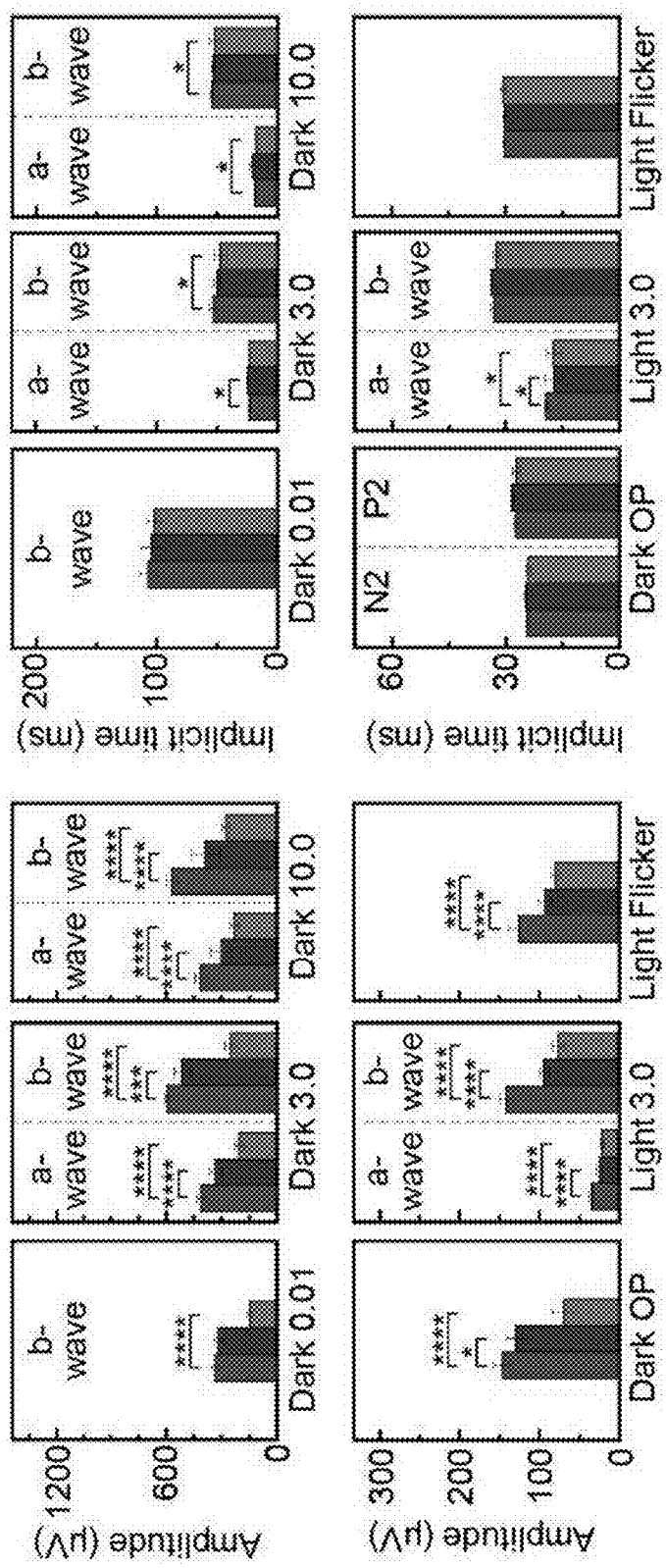

FIG. 5A shows representative measurement results of the standard full-field ERG signals that were sequentially measured using the device 100 (red lines) by comparison with the ERG-Jet lens (blue lines) and the DTL fiber (green lines). The ERG recordings by using the device 100 showed consistent results of the highest amplitudes throughout the entire testing period of each session (typically greater than 30 minutes), while providing better comfort of wear than other devices. FIG. 5B shows a summary of the average amplitudes (left column) and implicit times (right column) obtained from at least eight repeated recordings for each ERG protocol. The results obtained from a one-way analysis of variance (ANOVA) confirm that the amplitudes of the device 100 were significantly higher than those of other devices (p<0.0001), while the implicit times remained statistically unchanged.

The methods disclosed herein establish a platform technology that enables turning common commercially-available disposable SCLs 110 into a functional eye-wearable devices 100 tailored for ophthalmic ERG testing in human eyes. The resulting device 100 is thin and deformable, and can be printed on the SCL 110 without substantially altering the intrinsic lens properties in terms of biocompatibility, softness, oxygen permeability, transparency, wettability, and ergonomic curvature. A strategy that utilizes an electrochemical anchoring of the corneal sensor 102 to SCLs 110 provides a guideline to enhance the mechanical robustness and chemical stability, in order to meet the requirements for lens fitting, handling, cleaning, and disinfection.

The use of commercially available SCLs allows the device to form a conformal, seamless contact to a variety of corneal shapes, and therefore provides superior comfortability and on-eye safety compared to current clinical standards (e.g., the ERG-Jet lens and the Burian-Allen lens). The findings from the first-in-human validation study confirm the capability of the device in the high-fidelity recording of standard full-field ERG signals with a high signal-to-noise ratio. Importantly, the ERG recording is accomplished in a manner that allows for natural blinking and eye movements, without topical anesthesia or a speculum that is typically used in current ophthalmic examinations despite its adverse effects. Moreover, the fabrication of the device involves the use of a well-established DIW method that may facilitate the exploration of high-throughput batch production, potentially making the final product disposable and affordable for widespread adoption in the future.

The teachings disclosed herein enable turning commercial soft contact lenses into lifesaving diagnostic tools that can comfortably and accurately diagnose the status of ocular diseases, such as cataracts, diabetic retinopathy, and glaucoma, which are the most primary causes of vision loss. With these methods thin, flexible devices can be added onto commercial soft contact lenses without substantially altering the lens thickness, and not creating significant thickness differentials across the lenses, as otherwise they would perform differently. The use of the commercial soft contact lenses that are already well-established and widely prevalent allows these devices to take advantages from their intrinsic attributes in terms of biocompatibility, oxygen permeability, wettability, softness, and ergonomic curvature. These configurations allow the recording of ocular biosignals to occur in a continuous fashion, even whether or not the eyelids are closed, and thereby can eliminate the need for conventional use of corneal anesthesia and an auxiliary blepharostat for ophthalmic examinations. These teachings establish a foundation to significantly extend the functionality of existing soft contact lenses to far beyond traditional vision corrections, to many future potential applications such as continuous monitoring of biomarkers from tear fluids, controlled on-demand delivery of ocular drugs, eye-wearable night vision, head-up display, augmented reality, and eye-tracking controller, which greatly benefit ocular health, wellness, and disease prevention.

Although tosylate was used as the dopant for PEDOT in the investigations reported above, the invention encompasses the use of other dopants, in particular, other anionic dopants such as commonly-used sulfonates and sulfonic acid materials, the most common of which is poly(styrene sulfonate) (PSS), as well as other classes of materials including biologically-derived materials.

While the invention has been described in terms of specific or particular embodiments, it is apparent that other forms could be adopted by one skilled in the art. For example, the physical configuration of the eye-wearable device 100 could differ from that shown, and materials and processes/methods other than those noted could be used. Therefore, the scope of the invention is to be limited only by the following claims.

The invention claimed is:

1. A device comprising:
   a contact lens configured to be located and retained on a user's eye;
   a corneal sensor that includes a circular trace of conduction paths located at or near an outer peripheral edge of the contact lens, wherein the circular trace surrounds an unobstructed area at a center region of the contact lens;
   a conduction encapsulation layer around the entire surface of the conduction paths of the circular trace and that seamlessly penetrates the inner surface of the contact lens, the corneal sensor comprising silver flake-filled polystyrene-b-poly(ethylene-co-butylene)-b-polystyrene (AgSEBS) encased in the conduction encapsulation layer, and the conduction encapsulation layer comprising doped poly(3,4-ethylenedioxythiophene) (PEDOT); and
   a connection wire coupled to the corneal sensor and configured to electrically couple the corneal sensor to an external data acquisition system.

2. The device of claim 1, wherein the circular trace defines a circular serpentine pattern.

3. The device of claim 1, wherein the circular trace is stretched such that the circular trace accommodates interfacial stress of a curvilinear inner surface of the contact lens and thereby reduces surface discontinuity, and wherein the connection wire is an elastomeric connection wire.

4. The device of claim 1, wherein the circular trace is positioned on an inner surface of the contact lens configured to face the corneal surface of the user's eye during use.

5. The device of claim 4, wherein the connection wire penetrates through the contact lens from the inner surface of the contact lens to an outer surface of the contact lens opposite the inner surface of the contact lens to contact the corneal sensor.

6. The device of claim 1, wherein the conduction paths of the corneal sensor comprise an inner conduction path surrounded by an outer conduction path, wherein the inner conduction path formed by the AgSEBS and the outer conduction path comprises gold (Au).

7. The device of claim 1, wherein the connection wire comprises an elastomeric connection wire comprising silver flake-filled polystyrene-b-poly(ethylene-co-butylene)-b-polystyrene (AgSEBS) encased in fumed silica nanoparticle-filled polydimethylsiloxane (PDMS).

8. A method comprising:
   providing a glass substrate coated with a water-soluble layer;
   depositing elastomeric materials on the water-soluble layer of the glass substrate to simultaneously form a circular trace and a connection wire coupled to the circular trace, wherein the elastomeric materials includes silver flake-filled polystyrene-b-poly(ethylene-co-butylene)-b-polystyrene (AgSEBS) and at least one layer of the circular trace and at least one layer of the connection wire define an integral conduction path;
   removing the water-soluble layer with deionized water to separate the circular trace and the connection wire from the glass substrate;
   electroplating the circular trace with gold or an alloy thereof;
   transferring the circular trace to a curvilinear inner surface of a contact lens configured to face a user's eye when worn;
   feeding the connection wire through the inner surface of the contact lens and out of an outer surface of the contact lens; and
   performing electrochemical polymerization of a conducting polymer material over the circular trace to anchor the circular trace to the inner surface of the contact lens, the conducting polymer material being doped poly(3,4-ethylenedioxythiophene) (PEDOT) and the conducting polymer forming a conduction encapsulation layer around the entire surface of the circular trace;
   wherein the circular trace is configured to function as a corneal sensor and the connection wire is configured to couple the corneal sensor to an external data acquisition system.

9. The method of claim 8, further comprising locating the contact lens on a user's eye such that the corneal sensor contacts the corneal thereof and recording ERG signals with the external data acquisition system.

10. The method of claim 8, wherein the elastomeric materials include fumed silica nanoparticle-filled polydimethylsiloxane (PDMS).

11. The method of claim 8, further comprising stretching the circular trace when contacted to the curvilinear inner surface of the contact lens until it accommodates interfacial stress to reduce surface discontinuity.

12. The method of claim 8, wherein the circular trace defines a circular serpentine pattern.

13. A method comprising:
    providing a thin device that includes a sensor and a connection wire coupled to the sensor, the sensor having an inner conduction path formed of silver flake-filled polystyrene-b-poly(ethylene-co-butylene)-b-polystyrene (AgSEBS);
    transferring the sensor to a curvilinear inner surface of a contact lens configured to face a user's eye when worn;
    feeding the connection wire through the inner surface of the contact lens and out of an outer surface of the contact lens; and
    performing electrochemical polymerization of a conducting polymer material over the sensor to anchor the sensor to the inner surface of the contact lens, the conducting polymer material being doped poly(3,4-ethylenedioxythiophene) (PEDOT), and the conducting polymer forming a conduction encapsulation layer around the entire surface of the sensor;
    wherein the connection wire is configured to couple the sensor to an external electrical system.

14. The method of claim 13, wherein the sensor has a circular ring shaped body that is located at or near an outer peripheral edge of the contact lens such that the body surrounds an unobstructed area at a center region of the contact lens.

15. The method of claim 14, wherein the circular ring shaped body defines a circular serpentine pattern.

16. The method of claim 14, further comprising stretching the circular ring shaped body when contacted to the curvilinear inner surface of the contact lens until it accommodates interfacial stress to reduce surface discontinuity.

17. The method of claim 13, wherein the conduction encapsulation layer seamlessly penetrates the inner surface of the contact lens.

18. The method of claim 13, wherein the sensor includes an outer conduction path formed of gold (Au) surrounding the inner conduction path.

* * * * *